(12) United States Patent
Costantino et al.

(10) Patent No.: US 8,129,339 B2
(45) Date of Patent: Mar. 6, 2012

(54) MICROENCAPSULATION AND SUSTAINED RELEASE OF BIOLOGICALLY ACTIVE POLYPEPTIDES

(75) Inventors: Henry R. Costantino, Woodinville, WA (US); Joyce M. Hotz, Cincinnati, OH (US); James R. Dasch, Needham, MA (US); M. Gary I. Riley, Boston, MA (US); Paul A. Burke, Philadelphia, PA (US); Susan A. Steitz-Abadi, Barrington, RI (US); Stephen E. Zale, Hopkinton, MA (US)

(73) Assignee: Alkermes Pharma Ireland Limited, Athlone (IE)

(*) Notice: Subject to any disclaimer, the term of this patent is extended or adjusted under 35 U.S.C. 154(b) by 311 days.

(21) Appl. No.: 12/289,857

(22) Filed: Nov. 6, 2008

(65) Prior Publication Data

US 2009/0281034 A1 Nov. 12, 2009

Related U.S. Application Data

(63) Continuation of application No. 10/688,059, filed on Oct. 17, 2003, now Pat. No. 7,462,365.

(60) Provisional application No. 60/419,388, filed on Oct. 17, 2002.

(51) Int. Cl.
*A61K 38/00* (2006.01)
*A61K 38/28* (2006.01)
*A61P 5/50* (2006.01)
*A61P 3/08* (2006.01)
*A61P 3/10* (2006.01)
*A61P 7/12* (2006.01)

(52) U.S. Cl. .............................. 514/6.7; 514/6.8; 514/6.9

(58) Field of Classification Search .................. None
See application file for complete search history.

(56) References Cited

U.S. PATENT DOCUMENTS

| | | | |
|---|---|---|---|
| 3,523,906 A | 8/1970 | Vrancken et al. | |
| 3,691,090 A | 9/1972 | Kitajima et al. | |
| 3,737,337 A | 6/1973 | Schnoring et al. | |
| 3,891,570 A | 6/1975 | Fukushima et al. | |
| 3,960,757 A | 6/1976 | Morishita et al. | |
| 4,389,330 A | 6/1983 | Tice et al. | |
| 4,530,840 A | 7/1985 | Tice et al. | |
| 4,542,025 A | 9/1985 | Tice et al. | |
| 5,019,400 A | 5/1991 | Gombotz et al. | |
| 5,126,147 A | 6/1992 | Silvestri et al. | |
| 5,225,205 A | 7/1993 | Orsolini | |
| 5,336,505 A | 8/1994 | Ng et al. | |
| 5,385,887 A | 1/1995 | Yim et al. | |
| 5,424,286 A * | 6/1995 | Eng ................... | 514/2 |
| 5,578,567 A | 11/1996 | Cardinaux et al. | |
| 5,589,167 A | 12/1996 | Cleland et al. | |
| 5,610,159 A | 3/1997 | Moseley et al. | |
| 5,618,563 A | 4/1997 | Berde et al. | |
| 5,656,297 A | 8/1997 | Bernstein et al. | |
| 5,672,659 A | 9/1997 | Shalaby et al. | |
| 5,700,485 A | 12/1997 | Berde et al. | |
| 5,707,644 A | 1/1998 | Illum | |
| 5,834,428 A | 11/1998 | Drucker et al. | |
| 5,922,253 A | 7/1999 | Herbert et al. | |
| 5,922,340 A | 7/1999 | Berde et al. | |
| 5,981,719 A | 11/1999 | Woiszwillo et al. | |
| 6,024,983 A | 2/2000 | Tice et al. | |
| 6,046,187 A | 4/2000 | Berde et al. | |
| 6,096,728 A * | 8/2000 | Collins et al. .................. | 514/62 |
| 6,113,947 A | 9/2000 | Cleland et al. | |
| 6,190,702 B1 | 2/2001 | Takada et al. | |
| 6,203,813 B1 | 3/2001 | Gooberman | |
| 6,214,387 B1 | 4/2001 | Berde et al. | |
| 6,238,702 B1 | 5/2001 | Berde et al. | |
| 6,248,345 B1 | 6/2001 | Goldenheim et al. | |
| 6,369,116 B1 | 4/2002 | Wong et al. | |
| 6,426,339 B1 | 7/2002 | Berde et al. | |
| 6,465,425 B1 | 10/2002 | Tracy et al. | |
| 6,506,724 B1 | 1/2003 | Hiles et al. | |
| 6,749,866 B2 | 6/2004 | Bernstein et al. | |
| 7,164,005 B2 * | 1/2007 | Costantino et al. ........... | 530/350 |
| 7,462,365 B2 * | 12/2008 | Costantino et al. ........... | 424/468 |
| 2004/0028733 A1 | 2/2004 | Tracy et al. | |
| 2004/0047863 A1 | 3/2004 | Bendele et al. | |
| 2007/0027085 A1 | 2/2007 | Costantino et al. | |

FOREIGN PATENT DOCUMENTS

| | | |
|---|---|---|
| AU | B-81544/94 | 4/1997 |
| EP | 1 142 567 A2 | 10/2001 |
| WO | WO-96/34599 A1 | 11/1996 |
| WO | WO-97/44016 A1 | 11/1997 |
| WO | WO-99/01114 A1 | 1/1999 |

OTHER PUBLICATIONS

Andrews et al. Glucocorticoids and insulin resistance: old hormones, new targets. Clin Sci (Lond) 1999, vol. 96, No. 5, pp. 513-523.*

Creighton, Thomas E., Proteins: Structures and Molecular Principles, pp. 149-150 (published by W.H. Freeman and Company, NY, 1984).

Edwards et al., "Exendin-4 reduced fasting and postprandial glucose and decreases energy intake in healthy volunteers," Am. J. Physiol. Endocrinol. Metab., Jul. 2001, vol. 281: pp. E155-E161.

Elvassore et al., "Production of Insulin-Loaded Poly(Ethylene Glycol)/Poly(l-Lactide) (PEG/PLA) Nanoparticles by Gas Antisolvent Techniques," J. of Pharmaceutical Sci., 90(10): 1628 (Oct. 2001).

Haynes et al., "Neutralizing Anti-F Glycoprotein and Anti-Substance P Antibody Treatment Effectively Reduces Infection and Inflammation Associated with Respiratory Syncytial Virus Infection," Journal of Virology, 76(14): 6873-6881 (2002).

Kurt-Jones et al., "Pattern recognition receptors TLR4 and CD14 mediate response to respiratory syncytial virus," Nature Immunology, 1(5): 398-401 (2000).

(Continued)

*Primary Examiner* — Marcela M Cordero Garcia
(74) *Attorney, Agent, or Firm* — Covington & Burling LLP; Andrea G. Reister; Melody Wu

(57) ABSTRACT

The invention relates to compositions and methods for the sustained release of biologically active polypeptides. The sustained release compositions of this invention comprise a biocompatible polymer having dispersed therein a biologically active polypeptide, and a corticosteroid to modify the release profile and provide increased bioavailability.

6 Claims, 18 Drawing Sheets

OTHER PUBLICATIONS

Lee and Timasheff, "The Stabilization of Proteins by Sucrose," J. Biological Chem., 256(14): 7193-7201 (1981).

Lucke et al., "Peptide Acylation by Poly(a-Hydroxy Esters)," Pharmaceutical Research, 19(2): 175-181 (2002).

Taylor et al., "Continuous Subcutaneous Infusion of AC2993 (Synthetic Exendin-4) Provides Sustained Day-Long Glycemic Control to Patients with Type 2 Diabetes," Diabetes 51 (Suppl 2): A85 (Jun. 2002 Conference Abstract).

Drucker, "Glucagon-like peptides," Diabetes, 47: 159-169 (1998).

HCAPLUS abstract 1994:622315 (1994).

Medline abstract 2000463624 (Oct. 2000).

Noble, et al., "Insulin lispro: A fast-acting insulin analog," American Family Physician, 57(2) (Jan. 15, 1998), http://www.aafp.org/afp/980115ap/noble.html.

Renn, et al., "Characterization and cloning of tripeptidyl peptidase II from the fruit fly, *Drosophila melanogaster*," J. Biol. Chem., 273(30): 19173-19182 (1998).

Sansoni, et al., "Inhibition of antigen-presenting cell function by alendronate in vitro," J. Bone and Miner. Res., 10(11): 1719-1725 (1995).

Schacke, et al., "Mechanisms involved in the side effects of glucocorticoids," Pharmacology & Therapeutics, 96: 23-43 (2002).

Selander, et al., "Characteristics of clodronate-induced apoptosis in osteoclasts and macrophages," Mol. Pharmacol., 50(5): 1127-1138 (1996).

Spilizewski, et al., "The effect of hydrocortisone acetate loaded poly (DL-lactide) films on the inflammatory response," Journal of Controlled Release, 2: 197-203 (1985).

Weiss, et al., "Osteopontin is involved in the initiation of cutaneous contact hypersensitivity by inducing langerhans and dendritic cell migration to lymph nodes," J. Exp. Med., 194(9): 1219-1229 (2001).

Willi, et al., "Effective use of thiazolidinediones for the treatment of glucocorticoid-induced diabetes," Diabetes Research and Clinical Practice, 58: 87-96 (2002).

Zignani, et al., "A poly(ortho ester) designed for combined ocular delivery of dexamethasone sodium phosphate and 5-fluorouracil: subconjunctival tolerance and in vitro release," European Journal of Pharmaceutics and Biopharmaceutics, 50: 251-255 (2000).

* cited by examiner

MICROENCAPSULATION AND SUSTAINED RELEASE OF BIOLOGICALLY ACTIVE POLYPEPTIDES

RELATED APPLICATION(S)

This application claims the benefit of U.S. Provisional Application No. 60/419,388, filed Oct. 17, 2002.

The entire teachings of the above application(s) are incorporated herein by reference.

BACKGROUND OF THE INVENTION

Numerous proteins and peptides, collectively referred to herein as polypeptides, exhibit biological activity in vivo, which renders them useful as medicaments in therapy. Many illnesses or conditions which can be treated with a biologically active polypeptide, require administration of a constant or sustained level of medicament to provide the most effective prophylactic and/or therapeutic effects. As such, administration of biologically active polypeptides can require frequent subcutaneous injections, which result in fluctuating levels of medicament and poor patient compliance.

As an alternative, the use of biodegradable materials, such as polymers, encapsulating the medicament can be employed as a sustained delivery system. The use of biodegradable polymers, for example, in the form of microparticles or microcarriers, can provide a sustained release of medicament, by utilizing the inherent biodegradability of the polymer to control the release of the medicament thereby providing a more consistent, sustained level of medicament and improved patient compliance.

However, these sustained release devices can exhibit high initial bursts of medicament and minimal release thereafter, resulting in serum drug levels outside the therapeutic window and/or poor bioavailability of the medicament. In addition, the presence of polymer, physiological temperatures and body response to the sustained release composition can cause the medicament to be altered (e.g., degraded, aggregated) thereby interfering with the desired release profile for the medicament.

Further, methods used to form sustained release compositions can result in loss of activity of the medicament due to the instability of the medicament and the degradative effects of the processing steps. Degradative effects are particularly problematic when the medicament is a polypeptide.

Therefore, a need exists for a means of administering biologically active polypeptides in a sustained fashion wherein the amount of polypeptide delivered is at therapeutic levels, and retains activity and potency for the desired period of release.

SUMMARY OF THE INVENTION

The present invention is based upon the unexpected discovery that when a specific combination of excipients, namely a sugar and salting-out salt, are present in a sustained release composition comprising a biocompatible polymer and a biologically active polypeptide that an improved release profile of active agent is achieved. Most notably, sustained release compositions having this specific combination of excipients exhibit an increase of bioavailability of the polypeptide over compositions lacking the specific combination of excipients, thereby resulting in an improved sustained release composition which can deliver therapeutic levels of polypeptide for a desired period. In addition, the sustained release compositions having this specific combination of excipients can exhibit a reduced lag phase which can provide for a smoothing out of the release profile and can contribute to an increase in the amount of agent released.

This invention relates to compositions for the sustained release of biologically active polypeptides, and methods of forming and using said compositions for the sustained release of biologically active polypeptides. The sustained release compositions of this invention comprise a biocompatible polymer having dispersed therein, a biologically active polypeptide, a sugar and a salting-out salt.

The method of the invention, for forming a composition for the sustained release of biologically active polypeptide, includes dissolving a biocompatible polymer in a polymer solvent to form a polymer solution, and combining a biologically active polypeptide, sugar and salting-out salt with the polymer solution. The biologically active polypeptide, sugar and salting-out salt can be combined with the polymer solution either alone or in a premixed form. The biologically active polypeptide, sugar and salting-out salt can be combined with the polymer solution either as solids, liquids or suspensions. It is understood that the method of combining the polymer, active and excipients can be performed in any order.

The method of using the sustained release composition of the present invention comprises providing a therapeutically effective blood level of biologically active polypeptide, in a patient for a sustained period by administering to the patient a dose of the sustained release composition described herein.

In a particular embodiment, the sustained release composition has incorporated therein a hormone, particularly an anti-diabetic or glucoregulatory peptide, for example, GLP-1, GLP-2, exendin-3, exendin-4 or agonists, analogs or derivatives thereof and the composition is administered in a therapeutically effective amount to treat a patient suffering from diabetes mellitus, impaired glucose tolerance (IGT), obesity, cardiovascular (CV) disorder or any other disorder that can be treated by one of the above polypeptides or derivatives, analogs or agonists thereof.

The sustained release composition of the invention overcomes the problem of lack of acceptable bioavailability of the incorporated biologically active polypeptide which can occur when the specific combination of sugar and salting-out salt is not present in the sustained release composition. Further, loss of activity of the biologically active polypeptide due to instability and/or chemical interactions between the biologically active polypeptide and other components which are contained in or used in formulating the sustained release composition, can be minimized.

The advantages of the sustained release formulation for biologically active molecule as described herein include increased patient compliance and acceptance by eliminating the need for repetitive administration, increased therapeutic benefit by eliminating fluctuations in active agent concentration in blood levels by providing a desirable release profile, and a potential lowering of the total amount of biologically active polypeptide necessary to provide a therapeutic benefit by reducing these fluctuations.

DETAILED DESCRIPTION OF THE INVENTION

Figure 1:
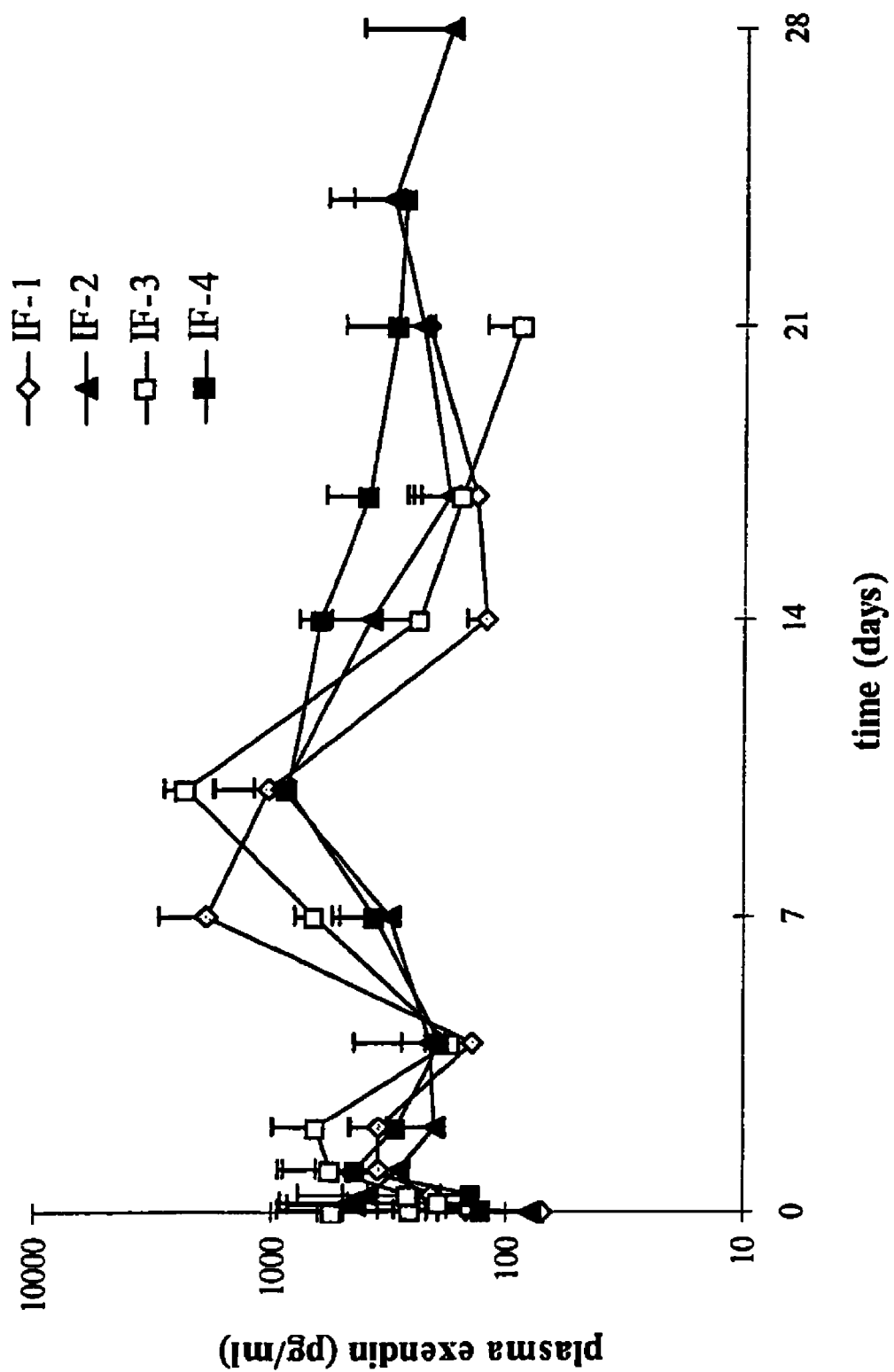
FIG. 1 a graph of plasma levels (pg/mL) in rats of exendin-4 versus time in days post administration for the selected microparticle formulations.

This invention relates to compositions for the sustained release of biologically active polypeptides, and methods of forming and using said compositions, for the sustained release of biologically active polypeptides. The sustained release compositions of this invention comprise a biocompatible polymer having dispersed therein, a biologically active polypeptide, a sugar and a salting-out salt.

The method of the invention, for forming a composition for the sustained release of biologically active polypeptide, includes dissolving a biocompatible polymer in a polymer solvent to form a polymer solution, and combining a biologically active polypeptide alone or in combination with other active ingredients, sugar and salting-out salt with the polymer solution. The biologically active polypeptide, sugar and salting-out salt can be combined with the polymer solution either alone or in a premixed form. The biologically active polypeptide, sugar and salting-out salt can be combined with the polymer solution either as solids, liquids or suspensions. It is understood, that the combination of the components of the composition can be achieved in any order.

The method of using the sustained release composition of the present invention comprises providing a therapeutically effective blood level of biologically active polypeptide, in a patient for a sustained period by administering to the patient a dose of the sustained release composition described herein.

In a particular embodiment, the sustained release composition comprises a biocompatible polymer, an antidiabetic or glucoregulatory polypeptide, a sugar and a salting-out salt. More specifically, the polypeptide is selected from GLP-1, GLP-2, exendin-3, exendin-4 or an analog, derivative or agonist thereof. Most specifically, the polypeptide is exendin-4. When the polypeptide is exendin-4, the sugar is preferably sucrose, mannitol or a combination thereof and the salting-out salt is preferably ammonium sulfate. This preferred combination in no way excludes other combinations of sugar or salt with exendin-4 and it is understood that other combinations are included.

In a particular embodiment, the sustained release composition comprises a biocompatible polymer, exendin-4, sucrose and a salting-out salt. The exendin-4 can be present in the composition at a concentration of about 0.01% to about 10% w/w based on the total weight of the final composition. In addition, the sucrose can be present in a concentration of about 0.01% to about 5% w/w of the dry weight of the composition. Further, the ammonium sulfate can be present in the sustained release composition at a concentration of about 0.01% to about 5% w/w of the final weight of the composition.

Salting-out salts, as that term is used herein, refers to salts which are in the Hofmeister series of precipitants of serum globulins (or "salting-out salts") as described in Thomas E. Creighton in *Proteins: Structures and Molecular Principles*, pp. 149-150 (published by W.H. Freeman and Company, New York). In general, the salting-out salts are known in the art as suitable for precipitating a protein, without denaturing the protein. Salting-out salts can also be described in terms of the "kosmotrope" and "chaotrope" properties of the constituent ions. The term kosmotrope generally refers to a solute that stabilizes proteins and chaotrope describes a solute that is destabilizing. Kosmotropic ions have a high charge density (e.g., $SO_4^{2-}$, $HPO_4^{2-}$, $Mg^{2+}$, $Ca^{2+}$, $Li^+$, $Na^+$ and $HPO_4^{2-}$) and chaotropic ions have a low charge density (examples include $H_2PO_4^-$, $HSO_4^-$, $HCO_3^-$, $I^-$, $Cl^-$, $NO_3^-$, $NH_4^+$, $Cs^+$, $K^+$, $[N(CH_3)_4]^+$). The salting out salt can also be described in terms of its ability to donate or accept protons, and as such acting as a base or acid. For instance, the salting out salt $(NH_4)_2SO_4$ provides an ammonium ion, and can act as an inorganic acid. When included in a polymeric microparticle such inorganic acids can modulate polymer degradation and effect release of incorporated agent. In certain embodiments, amino acids such as glycine which is considered in the art as a kosmotrope can be used as an alternative to the salting-out salt.

Suitable salting-out salts for use in this invention include, for example, salts containing one or more of the cations $Mg^{+2}$, $Li^+$, $Na^+$, $K^+$ and $NH_4^+$; and also containing one or more of the anions $SO_4^{-2}$, $HPO_4^{-2}$, acetate, citrate, tartrate, $Cl^-$, $NO_3^-$, $ClO_3^-$, $I^-$, $ClO_4^-$ and $SCN^-$.

The amount of salting-out salt present in the sustained release composition can range from about 0.01% (w/w) to about 50% (w/w), such as from about 0.01% to about 10% (w/w), for example from about 0.01% to about 5%, such as 0.1% to about 5% of the total weight of the sustained release composition. Combinations of two or more salting-out salts can be used. The amount of salting-out salt, when a combination is employed, is the same as the range recited above.

A sugar as defined herein, is a monosaccharide, disaccharide or oligosaccharide (from 3-10 monosaccharides) or a derivative thereof. For example, sugar alcohols of monosaccharides are suitable derivatives included in the present definition of sugar. As such, the sugar alcohol mannitol, for example, which is derived from the monosaccharide mannose is included in the definition of sugar as used herein.

Suitable monosaccharides include, but are not limited to, glucose, fructose and mannose. A disaccharide, as further defined herein, is a compound which upon hydrolysis yields two molecules of a monosaccharide. Suitable disaccharides include, but are not limited to, sucrose, lactose and trehalose. Suitable oligosaccharides include, but are not limited to, raffinose and acarbose.

The amount of sugar present in the sustained release composition can range from about 0.01% (w/w) to about 50% (w/w), such as from about 0.01% (w/w) to about 10% (w/w), such as from about 0.1% (w/w) to about 5% (w/w) of the total weight of the sustained release composition.

Alternatively, the amount of sugar present in the sustained release composition can be referred to on a weight ratio with the biologically active polypeptide. For example, the polypeptide and sugar can be present in a ratio from about 10:1 to about 1:10 weight:weight.

Combinations of two or more sugars can also be used. The amount of sugar, when a combination is employed, is the same as the ranges recited above.

Biologically active polypeptides as used herein collectively refers to biologically active proteins and peptides and the pharmaceutically acceptable salts thereof, which are in their molecular, biologically active form when released in vivo, thereby possessing the desired therapeutic, prophylactic and/or diagnostic properties in vivo. Typically, the polypeptide has a molecular weight between 500 and 200,000 Daltons.

Suitable biologically active polypeptides include, but are not limited to, glucagon, glucagon-like peptides such as, GLP-1, GLP-2, exendin-3, exendin-4 and analogs, agonists, and derivatives thereof, vasoactive intestinal peptide (VIP), immunoglobulins, antibodies, cytokines (e.g., lymphokines, monokines, chemokines), interleukins, macrophage activating factors, interferons, erythropoietin, nucleases, tumor necrosis factor, colony stimulating factors (e.g., G-CSF), insulin, enzymes (e.g., superoxide dismutase, plasminogen activator, etc.), tumor suppressors, blood proteins, hormones and hormone analogs and agonists (e.g., follicle stimulating hormone, growth hormone, adrenocorticotropic hormone, and luteinizing hormone releasing hormone (LHRH)), vaccines (e.g., tumoral, bacterial and viral antigens), antigens, blood coagulation factors, growth factors (NGF and EGF), gastrin, GRH, antibacterial peptides such as defensin, enkephalins, bradykinins, calcitonin and muteins, analogs, deletion and substitution variants and pharmaceutically acceptable salts of the foregoing.

Exendin-4 is a 39 amino acid polypeptide. The amino acid sequence of exendin-4 can be found in U.S. Pat. No. 5,424, 286 issued to Eng on Jun. 13, 1995, the entire content of which is hereby incorporated by reference. AC2993 is synonymous with the term exendin-4 simply referring to the synthetic exendin-4. Exendin-4 has been shown in humans and animals to stimulate secretion of insulin in the presence of elevated blood glucose concentrations, but not during periods of low blood glucose concentrations (hypoglycemia). It has also been shown to suppress glucagon secretion, slow gastric emptying and affect food intake and satiety, as well as other actions. As such, exendin-4 and analogs and agonists thereof can be useful in the treatment of diabetes mellitus, IGT, obesity, etc.

The amount of biologically active polypeptide, which is contained within the polymeric matrix of a sustained release composition, is a therapeutically, diagnostically or prophylactically effective amount which can be determined by a person of ordinary skill in the art, taking into consideration factors such as body weight, condition to be treated, type of polymer used, and release rate from the polymer.

Typically, the sustained release composition can contain from about 0.01% (w/w) to about 50% (w/w) of the biologically active polypeptide (total weight of composition). For example, the amount of biologically active polypeptide can be from about 0.1% (w/w) to about 30% (w/w) of the total weight of the composition. The amount of polypeptide will vary depending upon the desired effect, the planned release levels, and the time span over which the polypeptide will be released. A specific range of loading is between about 0.1% (w/w) to about 10% (w/w), for example, 0.5% (w/w) to about 5% (w/w).

In a further embodiment, the sustained release composition of the present invention can be coadministered with a corticosteroid. It has been shown herein that coadministration of the sustained release composition of the invention with a corticosteroid can further increase the bioavailablity of the biologically active polypeptide of the sustained release composition. Coadministration of a corticosteroid in combination with sustained release compositions is described in detail in U.S. patent application having U.S. Ser. No. 60/419,430 entitled, Method of Modifying the Release Profile of Sustained Release Compositions by Dasch et al. being filed concurrently, the entire content of which is hereby incorporated by reference.

Corticosteroids, as defined herein, refers to steroidal anti-inflammatory agents also referred to as glucocorticoids.

Suitable corticosteroids include, but are not limited to, 21-Acetoxypregnenolone, Alclometasone, Algestone, Amcinonide, Beclomethasone, Betamethasone, Budesonide, Chloroprednisone, Clobetasol, Clobetasone, Clocortolone, Cloprednol, Corticosterone, Cortisone, Cortivazol, Deflazacort, Desonide, Desoximetasone, Dexamethasone, Diflorasone, Diflucortolone, Difluprednate, Enoxolone, Fluazacort, Flucloronide, Flumethasone, Flunisolide, Flucinolone Acetonide, Fluocinonide, Fluocortin Butyl, Flucortolone, Fluorometholone, Fluperolone Acetate, Fluprednidene Acetate, Fluprednisolone, Flurandrenolide, Fluticasone Propionate, Formocortal, Halcinonide, Halobetasol Propionate, Halometasone, Halopredone Acetate, Hydrocortamate, Hydrocortisone, Loteprednol Etabonate, Mazipredone, Medrysone, Meprednisone, Methylprednisolone, Mometasone Furoate, Paramethasone, Prednicarbate, Prednisolone, Prednisolone 25-Diethylamino-acetate; Prednisolone Sodium Phosphate, Prednisone, Prednival, Prednylidene, Rimexolone, Tixocortol, Triamcinolone (all forms), for example, Triamcinolone Acetonide, Triamcinolone Acetonide 21-oic acid methyl ester, Triamcinolone Benetonide, Triamcinolone Hexacetonide, Triamcinolone Diacetate, pharmaceutically acceptable mixtures thereof and salts thereof and any other derivative and analog thereof.

In one embodiment, the corticosteroid can be co-incorporated into the sustained release composition comprising the biocompatible polymer and the biologically active polypeptide agent incorporated therein.

In another embodiment, the corticosteroid can be separately incorporated into a second biocompatible polymer. The second biocompatible polymer can be the same or different from the first biocompatible polymer which has the biologically active polypeptide agent incorporated therein.

In yet another embodiment, the corticosteroid can be present in an unencapsulated state but commingled with the sustained release composition. For example, the corticosteroid can be solubilized in the vehicle used to deliver the sustained release composition. Alternatively, the corticosteroid can be present as a solid suspended in an appropriate vehicle. Further, the corticosteroid can be present as a powder which is commingled with the sustained release composition.

It is understood that the corticosteroid is present in an amount sufficient to modify the release profile of the biologically active polypeptide from the sustained release composition. Modification of the release profile, refers to increased bioavailability of the biologically active polypeptide of the sustained release composition. Increased bioavailability refers to an increase in the bioavailability of the biologically active polypeptide from the sustained release composition when coadministered with a corticosteroid in comparison to the administration in the absence of corticosteroid over a time period beginning at two days post administration and ending at the targeted timepoint for the particular formulation.

As used herein, the term a or an refer to one or more.

As used herein, patient refers to a human.

As defined herein, a sustained release of biologically active polypeptide is a release of the polypeptide from the sustained release composition of the invention which occurs over a period which is longer than that period during which a biologically significant amount of the polypeptide would be available following direct administration of a solution of the polypeptide. It is preferred that a sustained release be a release which occurs over a period of at least about one week, such as at least about two weeks, at least about three weeks or at least about four weeks. The sustained release can be a continuous or a discontinuous release, with relatively constant or varying rates of release. The continuity of release and level of release can be affected by the type of polymer composition used (e.g., monomer ratios, molecular weight, block composition, and varying combinations of polymers), polypeptide loading, and/or selection of excipients to produce the desired effect.

As used herein, a therapeutically effective amount, prophylactically effective amount or diagnostically effective amount is the amount of the sustained release composition needed to elicit the desired biological response following administration.

Polymers suitable to form the sustained release composition of this invention are biocompatible polymers which can be either biodegradable or non-biodegradable polymers or blends or copolymers thereof. A polymer is biocompatible if the polymer and any degradation products of the polymer are non-toxic to the recipient and also possess no significant deleterious or untoward effects on the recipient's body, such as an immunological reaction at the injection site.

Biodegradable, as defined herein, means the composition will degrade or erode in vivo to form smaller units or chemical species. Degradation can result, for example, by enzymatic, chemical and physical processes. Suitable biocompatible, biodegradable polymers include, for example, poly(lactides), poly(glycolides), poly(lactide-co-glycolides), poly(lactic acid)s, poly(glycolic acid)s, polycarbonates, polyesteramides, polyanydrides, poly(amino acids), polyorthoesters, poly(dioxanone)s, poly(alkylene alkylate)s, copolymers or polyethylene glycol and polyorthoester, biodegradable polyurethane, blends thereof, and copolymers thereof.

Suitable biocompatible, non-biodegradable polymers include non-biodegradable polymers selected from the group consisting of polyacrylates, polymers of ethylene-vinyl acetates and other acyl substituted cellulose acetates, non-degradable polyurethanes, polystyrenes, polyvinylchloride, polyvinyl flouride, poly(vinyl imidazole), chlorosulphonate polyolefins, polyethylene oxide, blends thereof, and copolymers thereof.

Acceptable molecular weights for polymers used in this invention can be determined by a person of ordinary skill in the art taking into consideration factors such as the desired polymer degradation rate, physical properties such as mechanical strength, end group chemistry and rate of dissolution of polymer in solvent. Typically, an acceptable range of molecular weight is of about 2,000 Daltons to about 2,000,000 Daltons. In a preferred embodiment, the polymer is biodegradable polymer or copolymer. In a more preferred embodiment, the polymer is a poly(lactide-co-glycolide) (hereinafter "PLG") with a lactide:glycolide ratio of about 1:1 and a molecular weight of about 5,000 Daltons to about 70,000 Daltons. In an even more preferred embodiment, the molecular weight of the PLG used in the present invention has a molecular weight of about 5,000 Daltons to about 50,000 Daltons.

The sustained release composition of this invention can be formed into many shapes such as a film, a pellet, a cylinder, a disc or a microparticle. A microparticle, as defined herein, comprises a polymer component having a diameter of less than about one millimeter and having biologically active polypeptide dispersed or dissolved therein. A microparticle can have a spherical, non-spherical or irregular shape. Typically, the microparticle will be of a size suitable for injection. A typical size range for microparticles is 1000 microns or less. In a particular embodiment, the microparticle ranges from about one to about 180 microns in diameter.

Bioavailability, as that term is used herein, refers to the amount of therapeutic that reaches the general circulation. That is, the calculated Area Under the Curve (AUC) for the release profile of a particular polypeptide during the time period starting at post administration and ending at a predetermined time point. As is understood in the art, the release profile is generated by graphing the serum levels of a biologically active agent in a subject (Y-axis) at predetermined time point (X-axis). Bioavailability is often referred to in terms of % Bioavailability, which is the bioavailablity achieved for a particular polypeptide following administration of a sustained release composition divided by the bioavailability achieved for a particular polypeptide following administration of the same dose of drug intravenously multiplied by 100.

Increased bioavailability as that term is used herein refers to an increase in the bioavailability of a biologically active polypeptide agent from a sustained release composition when coadministered with a corticosteroid in comparison to the administration in the absence of corticosteroid over a time period beginning post administration and ending at the targeted timepoint for the particular formulation.

A modification of the release profile can be confirmed by appropriate pharmacokinetic monitoring of the patient's serum for the presence of the biologically active polypeptide agent. For example, specific antibody-based testing (e.g., ELISA and IRMA), as is well known in the art, can be used to determine the concentration of certain biologically active polypeptide agents in the patient's serum. An example of such testing is described herein for exendin-4.

Pharmacodynamic monitoring of the patient to monitor the therapeutic effects of the agent upon the patient can be used to confirm retention of the biologically activity of the released agent. Methods of monitoring pharmacodynamic effects can be selected based upon the biologically active polypeptide agent being administered using widely available techniques.

A number of methods are known by which sustained release compositions (polymer/biologically active polypeptide matrices) of the invention can be formed. In many of these processes, the material to be encapsulated is dispersed in a solvent containing a wall forming material (e.g., biocompatible polymer). At a single stage of the process, solvent is removed and thereafter the microparticle product is obtained.

Methods for forming a composition for the sustained release of biologically active polypeptide agent are described in U.S. Pat. No. 5,019,400, issued to Gombotz et al., and issued U.S. Pat. No. 5,922,253 issued to Herbert et al. the teachings of which are incorporated herein by reference in their entirety.

In this method, a mixture comprising a biologically active polypeptide, a biocompatible polymer and a polymer solvent is processed to create droplets, wherein at least a significant portion of the droplets contains polymer, polymer solvent and the biologically active agent. These droplets are then frozen by a suitable means. Examples of means for processing the mixture to form droplets include directing the dispersion through an ultrasonic nozzle, pressure nozzle, Rayleigh jet, or by other known means for creating droplets from a solution.

Means suitable for freezing droplets include directing the droplets into or near a liquified gas, such as liquid argon or liquid nitrogen to form frozen microdroplets which are then separated from the liquid gas. The frozen microdroplets are then exposed to a liquid or solid non-solvent, such as ethanol, hexane, ethanol mixed with hexane, heptane, ethanol mixed with heptane, pentane or oil.

The solvent in the frozen microdroplets is extracted as a solid and/or liquid into the non-solvent to form a polymer/active agent matrix comprising a biocompatible polymer and a biologically active agent. Mixing ethanol with other non-solvents, such as hexane, heptane or pentane, can increase the rate of solvent extraction, above that achieved by ethanol alone, from certain polymers, such as poly(lactide-co-glycolide) polymers.

A wide range of sizes of sustained release compositions can be made by varying the droplet size, for example, by changing the ultrasonic nozzle diameter. If the sustained release composition is in the form of microparticles, and very large microparticles are desired, the microparticles can be extruded, for example, through a syringe directly into the cold liquid. Increasing the viscosity of the polymer solution can also increase microparticle size. The size of the microparticles which can be produced by this process ranges, for example, from greater than about 1000 to about 1 micrometers in diameter.

Yet another method of forming a sustained release composition, from a suspension comprising a biocompatible polymer and a biologically active agent, includes film casting, such as in a mold, to form a film or a shape. For instance, after putting the suspension into a mold, the polymer solvent is then removed by means known in the art, or the temperature of the polymer suspension is reduced, until a film or shape, with a consistent dry weight, is obtained.

A further example of a conventional microencapsulation process and microparticles produced thereby is disclosed in U.S. Pat. No. 3,737,337, incorporated by reference herein in its entirety, wherein a solution of a wall or shell forming polymeric material in a solvent is prepared. The solvent is only partially miscible in water. A solid or core material is dissolved or dispersed in the polymer-containing mixture and, thereafter, the core material-containing mixture is dispersed in an aqueous liquid that is immiscible in the organic solvent in order to remove solvent from the microparticles.

Another example of a process in which solvent is removed from microparticles containing a substance is disclosed in U.S. Pat. No. 3,523,906, incorporated herein by reference in its entirety. In this process a material to be encapsulated is emulsified in a solution of a polymeric material in a solvent that is immiscible in water and then the emulsion is emulsified in an aqueous solution containing a hydrophilic colloid. Solvent removal from the microparticles is then accomplished by evaporation and the product is obtained.

In still another process as shown in U.S. Pat. No. 3,691,090, incorporated herein by reference in its entirety, organic solvent is evaporated from a dispersion of microparticles in an aqueous medium, preferably under reduced pressure.

Similarly, the disclosure of U.S. Pat. No. 3,891,570, incorporated herein by reference in its entirety, shows a method in which solvent from a dispersion of microparticles in a polyhydric alcohol medium is evaporated from the microparticles by the application of heat or by subjecting the microparticles to reduced pressure.

Another example of a solvent removal process is shown in U.S. Pat. No. 3,960,757, incorporated herein by reference in its entirety.

Tice et al., in U.S. Pat. No. 4,389,330, describe the preparation of microparticles containing an active agent by a method comprising: (a) dissolving or dispersing an active agent in a solvent and dissolving a wall forming material in that solvent; (b) dispersing the solvent containing the active agent and wall forming material in a continuous-phase processing medium; (c) evaporating a portion of the solvent from the dispersion of step (b), thereby forming microparticles containing the active agent in the suspension; and (d) extracting the remainder of the solvent from the microparticles.

A suitable polymer solution contains between about 1% (w/v) and about 30% (w/v) of a suitable biocompatible polymer, wherein the biocompatible polymer is typically dissolved in a suitable polymer solvent. Preferably, a polymer solution contains about 2% (w/v) to about 20% (w/v) polymer.

A suitable polymer solvent, as defined herein, is a solvent in which the polymer is soluble, in which some, none, or all of the other components are soluble and in which the other components are non-reactive. Examples of suitable polymer solvents include polar organic liquids, such as methylene chloride, chloroform, ethyl acetate, methyl acetate, hexafluoroisopropanol, acetone, dimethylsulfoxide and combinations thereof.

Further, excipients can be present in the sustained release composition. The excipients can be added to maintain the potency of the biologically active polypeptide agent over the duration of release and/or modify polymer degradation. Suitable excipients include, for example, buffer salts, carbohydrates, metal cations, amino acids, fatty acids, surfactants, and bulking agents, and are known to those skilled in the art. An acidic or a basic excipient is also suitable. The amount of excipient used is based on ratio to the biologically active polypeptide agent, on a weight basis and can be determined by one of skill in the art using available methods.

Buffer salt, as defined herein is the salt remaining following removal of solvent from a buffer. Buffers are solutions containing either a weak acid and a related salt of the acid, or a weak base and a salt of the base. Buffers can maintain a desired pH to assist in stabilizing the formulation. This maintenance of pH can be afforded during processing, storage and/or release. For example, the buffer can be monobasic phosphate salt or dibasic phosphate salt or combinations thereof or a volatile buffer such as ammonium bicarbonate. Other buffers include, but are not limited to, acetate, citrate, succinate and amino acids such as glycine, arginine and histidine. The buffer when present in the final sustained release composition can range from about 0.01% to about 10% of the total weight. In a preferred embodiment, the buffer salt is a sodium acetate salt.

A surfactant can be present in the sustained release composition. The surfactant can act to further modify release of the biologically active polypeptide from the polymer matrix, or can act to further stabilize the biologically active polypeptide or a combination thereof. The presence of surfactant can in some instances assist in minimizing adsorption of the biologically active polypeptide to the biocompatible polymer. The amount of surfactant present in the sustained release composition can range from about 0.1% w/w to about 50% w/w of the dry weight of the composition.

Surfactants, as the term is used herein refers to any substance which can reduce the surface tension between immiscible liquids. Suitable surfactants which can be added to the sustained release composition include polymer surfactants, such as nonionic polymer surfactants, for example, poloxamers, polysorbates, polyethylene glycols (PEGs), polyoxyethylene fatty acid esters, polyvinylpyrrolidone and combinations thereof. Examples of poloxamers suitable for use in the invention include poloxamer 407 sold under the trademark PLURONIC® F127, and poloxamer 188 sold under the trademark PLURONIC® F68, both available from BASF Wyandotte. Examples of polysorbates suitable for use in the invention include polysorbate 20 sold under the trademark TWEEN® 20 and polysorbate 80 sold under the trademark TWEEN® 80. Cationic surfactants, for example, benzalkonium chloride, are also suitable for use in the invention. In addition, bile salts, such as deoxycholate and glycocholate are suitable as surfactants based on their highly effective nature as detergents.

Bulking agents typically comprise inert materials. Suitable bulking agents are known to those skilled in the art.

A metal cation component which is dispersed within the polymer matrix can also be used as an optional excipient. This metal cation component acts to further modulate the release of polypeptide and is not complexed with the polypeptide. A metal cation component used in modulating release typically comprises at least one type of multivalent metal cation. Examples of metal cation components suitable to modulate protein release include or contain, for example, $Mg(OH)_2$, $MgCO_3$ (such as $4MgCO_3 \cdot Mg(OH)_2 \cdot 5H_2O$), $Zn(OAc)_2$, $ZnSO_4$ and $ZnCl_2$. A suitable ratio of metal cation component to polymer is between about 1:99 to about 1:2 by weight. The optimum ratio depends upon the polymer and the metal cation component utilized. A polymeric matrix containing a dispersed metal cation component to modulate the release of a biologically active agent from the polymeric matrix is further described in U.S. Pat. No. 5,656,297 and co-pending U.S. patent application Ser. No. 08/727,531, the teachings of both of which are incorporated herein by reference in their entirety.

Detailed procedures for microparticle formation are set forth in the Working Examples.

Without being bound by a particular theory it is believed that the release of the biologically active polypeptide, can occur by two different mechanisms. First, the biologically active polypeptide can be released by diffusion through aqueous filled channels generated in the polymeric matrix, such as by the dissolution of the polypeptide, or by voids created by the removal of the polymer solvent during the preparation of the sustained release composition. A second mechanism is the release of the polypeptide due to degradation of the polymer. The rate of degradation can be controlled by changing polymer properties that influence the rate of hydration of the polymer. These properties include, for instance, the ratio of different monomers, such as lactide and glycolide, comprising a polymer; the use of the L-isomer of a monomer instead of a racemic mixture; and the molecular weight of the polymer. These properties can affect hydrophilicity and crystallinity, which control the rate of hydration of the polymer. By altering the properties of the polymer, the contributions of diffusion and/or polymer degradation to release can be controlled. For example, increasing the glycolide content of a poly(lactide-co-glycolide) polymer and/or decreasing the molecular weight of the polymer can enhance the hydrolysis of the polymer and thus, provides an increased rate of release of protein due to polymer erosion.

In addition, the rate of polymer hydrolysis is increased in non-neutral pH. Therefore, an acidic or a basic excipient such as an inorganic acid or inorganic base can be added to the polymer solution, used to form the microparticle, to alter the polymer erosion rate The composition of this invention can be administered to a human, or other animal, by injection, implantation (e.g., subcutaneously, intramuscularly, intraperitoneally, intracranially, and intradermally), administration to mucosal membranes (e.g., intranasally, intravaginally, intrapulmonary or by means of a suppository), or in situ delivery (e.g., by enema or aerosol spray) to provide the desired dosage of biologically active polypeptide based on the known parameters for treatment with such protein of the various medical conditions.

The sustained release composition can be administered using any dosing schedule which achieves the desired therapeutic levels for the desired period of time. For example, the sustained release composition can be administered and the patient monitored until levels of the drug being delivered return to baseline. Following a return to baseline, the sustained release composition can be administered again. Alternatively, the subsequent administration of the sustained release composition can occur prior to achieving baseline levels in the patient.

For example, when the sustained release composition has incorporated therein a hormone, particularly an anti-diabetic or glucoregulatory peptide, for example, GLP-1, GLP-2, exendin-3, exendin-4 or agonists, analogs or derivatives thereof and the composition is administered in a therapeutically effective amount to treat a patient suffering from diabetes mellitus, impaired glucose tolerance (IGT), obesity, cardiovascular (CV) disorder or any other disorder that can be treated by one of the above polypeptides or derivatives, analogs or agonists thereof.

Other conditions which can be treated by administering the sustained release composition of the invention include Type I and Type II diabetes which can be treated with sustained release composition having insulin incorporated therein. In addition, when the incorporated polypeptide is FSH or analogs thereof the sustained release composition can be used to treat infertility. In other instances, the sustained release composition can be used to treat Multiple Sclerosis when the incorporated polypeptide is beta interferon or a mutein thereof. As can be realized, the sustained release composition can be to treat disease which respond to administration of a give polypeptide.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and scope of the invention be embraced by the defined claims.

The invention will now be further and specifically described by the following examples.

Exemplifications

Microparticle Preparation

The sustained release compositions described herein were prepared by any of emulsion, coacervation, and cryogenic microencapsulation techniques. The general process associated with each technique is described below.

Coacervation—W/O/O Process

The coacervation process, also referred to herein as a water-oil-oil (W/O/O) process, requires formation of a water-in-oil emulsion with aqueous drug and organic polymer solutions. An oil, typically a silicone oil, was then added to the water-in-oil emulsion to induce phase separation and to precipitate the polymer. The embryonic microparticles were then quenched in a solvent that removes the oil and polymer solvent.

Exendin-4 was encapsulated in PLG polymer using a water-oil-oil (W/O/O) emulsion system. The initial embryonic microparticles were formed in a W/O/O inner emulsion step after which they were subjected to coacervation and hardening steps. The microparticles were collected, dried and filled into vials. Further details of each step in the complete process is set forth below.

Inner Emulsion Formation

A water-in-oil emulsion was created using sonication. The water phase of the emulsion contained dissolved exendin-4 and various excipients in water. Typically, sucrose and ammonium sulfate were present as excipients but other excipients and combinations of excipients were investigated. The PLG phase contained polymer dissolved in methylene chloride.

Coacervation Formation

Coacervation was induced by adding silicone oil at a controlled rate to the inner emulsion with agitation, forming embryonic microparticles. The embryonic microparticles formed were relatively soft and required hardening.

Microparticle Hardening

The embryonic microparticles were added to a heptane/ethanol solvent mixture with gentle agitation. The solvent mixture hardened the embryonic microparticles. After hardening for about one hour at about 3° C., the solvent mixture was decanted and pure heptane was added at 3° C. and mixed for about one hour.

Microparticles Drying and Collection

After the hardening step, the microparticles were transferred and collected on a fine mesh pore-plate inside a drying chamber. A final heptane rinse of the hardening vessel was performed. The microparticles were dried with nitrogen gas over a four-day period with temperature ramping from about 3° C. to about 38° C.

In general, PLG was dissolved in methylene chloride. The inner water phase was prepared by dissolving the exendin-4, sucrose and ammonium sulfate in water or an aqueous buffer. The aqueous solution was then injected into the polymer solution while probe sonicating. The resultant water/oil emulsion was then added to an emulsion reactor. Silicone oil (350 centiStokes) was slowly added to the reactor via peristaltic pump with stirring at about 1000 rpm. The mixture was then added to n-heptane. After stirring for about two hours, the microparticles were isolated by filtration and vacuum dried overnight.

Emulsion Process—W/O/W Process

The emulsion process is also referred to as a water-oil-water (W/O/W) process. Briefly, an aqueous solution of drug was dispersed in a polymer solution which was then emulsified in an outer aqueous phase (e.g., PVA). The microparticles were then hardened in an aqueous quench.

In a typical experiment, PLG (1.96 g) was dissolved in methylene chloride (22.5 g) and drug (e.g., exendin-4) was dissolved in water (20 mg exendin-4 in 1.75 g water). The drug solution was then drawn up in a syringe and injected into the polymer solution while it was probe sonicated. The resultant W/O emulsion was then quickly added to an emulsion reactor containing 125 g aqueous 5% polyvinyl alcohol (PVA). The stir rate of the reactor was set to about 800 RPM. The mixture was stirred for about 1.5 minutes and then added to a water quench (2.8 L at 10° C.). After about two hours in the quench, the hardened microparticles were isolated by filtration and vacuum dried overnight.

Cryogenic Process

The cryogenic process used atomization to form droplets of polymer solution containing drug. Embryonic microparticles were then frozen in liquid nitrogen and the polymer solvent was removed through a subsequent ethanol extraction technique.

The cryogenic processing to produce microparticles included two steps: (1) the production of a lyophilizate; and (2) microencapsulation using a low-temperature, non-aqueous technique. Lyophilizates were formulated by atomizing a mixture of drug and excipient using a two-fluid nozzle, freezing the atomized droplets and drying the frozen droplets using lyophilization. It is understood that any suitable methods of drying known in the art can be employed. Specifically, frozen droplets were dried for about 7 days at a primary drying condition of −26° C. shelf and 96 mTorr chamber pressure followed by secondary drying for an additional 3 days at about 20° C. and 0 mTorr.

Exendin-4 containing microparticles were produced with the cryogenic, non-aqueous process, all at a nominal target load of 1% drug. Lyophilizates were suspended in an organic solution consisting of 6% 4A PLG dissolved in methylene chloride. This suspension was sonicated for about 4 minutes on ice, and then the suspension was atomized using a sonication nozzle and frozen by contacting with liquid nitrogen layered over a bed of frozen ethanol. The sample was warmed to −80° C. in order to allow for microparticle hardening and extraction of solvent. The microparticles were then filtered and dried.

Solid/Oil/Water (S/O/W) and Solid/Oil/Oil (S/O/O) Processes

Solid drug was also encapsulated using modified versions of the emulsion and coacervation processes described above. These modified processes are referred to solid/oil/water (S/O/W) and solid/oil/oil (S/O/O).

For example, solid exendin-4 was suspended in methylene chloride containing 6% PLG and sonicated for about four minutes on ice. Subsequent processing was conducted in a manner analogous to either the W/O/O or W/O/W methods.

Polymer:

Examples of specific PLG polymers suitable for use are listed below. All of the polymers employed in the following examples are set forth in the list and all listed polymers were purchased from Alkermes, Inc. of Cincinnati, Ohio and can be described as follows:

Polymer 2A: Poly(lactide-co-glycolide); 50:50 lactide:glycolide ratio; 12.3 kD Mol. Wt.; IV=0.15 (dL/g).

Polymer 2A-1: Poly(lactide-co-glycolide); 65:35 lactide:glycolide ratio; 16 kD Mol. Wt.; IV=0.19 (dL/g).

Polymer 2.5A: Poly(lactide-co-glycolide); 50:50 lactide: glycolide ratio; 25 kD Mol. Wt.; IV=0.24 (dL/g).

Polymer 3A: Poly(lactide-co-glycolide); 50:50 lactide:glycolide ratio; 47 kD Mol. Wt.; IV=0.38 (dL/g).

Polymer 3.5A: Poly(lactide-co-glycolide); 50:50 lactide: glycolide ratio; Mol. Wt., Not Determined; IV=0.42 (dL/g).

Polymer 4A: Poly(lactide-co-glycolide); 50:50 lactide:glycolide ratio; Mol. Wt. 45-64 kD; IV=0.45-0.47 (dL/g).

Polymer 4A-1: Poly(lactide-co-glycolide); 65:35 lactide: glycolide ratio; Mol. Wt. 53 kD; IV=0.43 (dL/g).

PURIFICATION OF PLG: It is known in the art (See, for example, Peptide Acylation by Poly($\alpha$-Hydroxy Esters) by Lucke et al., Pharmaceutical Research, Vol. 19, No. 2, p. 175-181, February 2002) that proteins and peptides which are incorporated in PLG matrices can be undesirably altered (e.g., degraded or chemically modified) as a result of interaction with degradation products of the PLG or impurities remaining after preparation of the polymer. As such, the PLG polymers used in the preparation of the majority of microparticle formulations described herein, were purified prior to preparation of the sustained release compositions using art recognized purification methods.

Methods of Analysis

The following methods were employed to analyze samples produced during the production and characterization of the microparticles described herein. For example, the bulk polypeptide can be analyzed, lyophilizates of the polypeptide can be analyzed, polypeptide extracted from the microparticles can be analyzed, as well as polypeptide released from the microparticles.

Exendin-4 Analysis

Analytical tests for purity, quantitation and identification of exendin-4 are as follows.

Reversed Phase-HPLC (RP-HPLC)

RP-HPLC was used to separate native exendin-4 from oxidized and truncated peptide. The relative amount of native exendin was reported as a percent of total absorption by UV; both 214 nm and 280 nm can be used for this purpose. The total peak area of all UV absorption impurities was used to define percent (%) purity of native exendin-4 and any impurities $\geq$0.1% of total AUC. Impurities are defined by their relative retention time compared to native AC2993 (RRT=1.00).

Samples were injected onto a C18 column (150 mm×4.6 mm), temperature-controlled at 40° C. The method was performed using gradient conditions with water and acetonitrile acidified with 0.1% TFA. The run time for the method was about 40 minutes per injection. The method was used to determine drug integrity.

Microsphere Characterization

Exendin-4 microspheres were routinely characterized with respect to drug content, particle size, residual solvents, initial in vitro release, and PK characteristics in rats. Drug was extracted to obtain a preliminary assessment of exendin-4 purity post-encapsulation in selected batches.

Particle Size Determination

The particle size distributions of the microparticle formulations described herein were determined with a Coulter LS 230 instrument employing laser diffraction technique equipped with the micro volume module. Generally, microparticles were suspended in an appropriate vehicle and subjected to analysis according to manufacturer's instructions. Mass median diameter, 10% greater than (microns), and 90% greater than (microns) were determined.

Load of Exendin-4

The exendin-4 content of bulk microparticles was determined by total nitrogen analysis using in an Exeter Analytical, model 240×A or XAI 240 nitrogen analyzer. Samples (5 mg) were combusted at 980° C. to produce carbon dioxide, nitrogen, and nitrogen oxides. The amount of exendin-4 present was determined based on the nitrogen content and the theoretical nitrogen content of exendin-4 (based on chemical formula of exendin-4, $C_{184}H_{282}N_{50}O_{60}S$).

Alternatively, following extraction, exendin-4 was quantified using Size-Exclusion Chromatograpy (SEC). The method uses a silica-based TSK-GEL SW column, isocratic elution with 0.1% TFA in water/acetonitrile mobile phase, and UV absorption at 280 m Size Exclusion Chromatography (SEC) was employed to quantify drug load following extraction from the microparticles. SEC was conducted on a silica-based TSK-GEL SW column available from Tosoh Biosep (Cat. #: 08540). The flow rate was 0.8 mL/min with a column load of about 10 µL containing about 0.2 mg/mL drug and a detector setting of 280 nm. The elution system was isocratic using 0.1% TFA in water/acetonitrile mobile phase.

Exendin-4 was extracted from the microparticles and the polymer was removed prior to determining the integrity, purity and identity of exendin-4. Briefly, the microparticles were dissolved in methylene chloride and the extracted exendin-4 was collected on a 0.1 µm filter, dried and then reconstituted in acetate buffer.

Residual Solvents

A single method was used for quantitation of heptane and methylene chloride. The equipment consisted of an HP 5890 Series 2 gas chromatograph with an Rtx 1301, 30 m×0.53 mm column. About 130 mg microparticles were dissolved in 10 ml N,N-dimethylformamide. Propyl acetate was used as the internal standard. The sample preparation was adjusted so that concentrations of methylene chloride as low as 0.03% can be quantitated.

In Vitro Initial Release

The initial release of exendin-4 was determined by measuring the concentration of exendin-4 after 24 hours. Typically, microparticles were incubated in isotonic, physiologic media (pH 7.4) at about 37° C. for about 24 hours. Exendin-4 concentration was determined using appropriate methods such as SEC and RP-HPLC. In vitro initial release of about 0.1% can be quantitated employing such methods.

Animal Studies

All pharmacokinetic (PK) studies described herein were conducted in adult male Sprague-Dawley rats weighing approximately 450±50 g (age 12-13 weeks).

For I.V. bolus studies, all animals were fully anesthetized with 5% halothane and a skin incision was made superior to the jugular vein. A dose of 30 g of exendin-4 per rat was administered into the jugular vein and the incision was closed with wound clips. Blood samples were collected via lateral tail vein 5, 10, 20, 30, 60, 90, 120, 150, 180, 240, 300 and 360 minutes post-dose.

For PK characterization of the microparticle formulations, each animal received a subcutaneous injection of microparticles suspended in diluent (3% carboxymethylcellulose, 0.9% NaCl, 0.1% Tween 20) to the inter-scapular region. Generally, the dose was approximately 0.9 mg exendin-4 per rat and the injection volume was 0.75 mL. Blood samples were collected via lateral tail vein at 2, 4, 6, 10, 24 hours post dose, and typically at 2, 4, 7, 19, 14, 17, 21, 24 and 28 days post-dose. Blood samples were immediately placed in MICROTAINER® tubes containing EDTA and centrifuged at about 14,000×g for about two minutes. Plasma was then transferred to MICROTAINER® tubes without additive and stored at −70° C. until time of assay. IRMA was used to determine plasma exendin concentrations.

In Vivo Release-IRMA

The method for quantifying exendin-4 in plasma is a sandwich immunoassay, with the analyte captured by a solid phase monoclonal antibody EXE4:2-8.4 and detected by the radio-iodinated monoclonal antibody GLP-1:3-3. Counts bound are quantitated from a standard calibration curve. This assay is specific for exendin-4 and does not detect exendin-4 (3-39) a major metabolite or GLP-1. A typical standard curve range is 30 pg/mL to 2000 pg/mL depending on the age of the tracer antibody.

Microparticle Characteristics

For all microparticle formulations which were prepared herein, a W/O/O process was employed. The inner phase was either water or sodium acetate buffer at a selected concentration and pH. The amount of exendin-4 and excipients present in the prepared formulations is expressed as a % (w/w) based on the final weight of the sustained release composition. The % (w/w) is a nominal percentage, except were indicated.

Discovery of Initial Formulations (IF)

As a result significant research, it was discovered that Initial Formulations 1-4 in Table 1 (IF-1, IF-2, IF-3 and IF-4) provided a desired release profile for exendin-4. For example, the Initial Formulations achieved a release of therapeutic levels of exendin-4 for about 3-4 weeks with minimal initial release. The Initial Formulations were prepared using the W/O/O process described above. The inner water emulsion containing exendin-4 was formulated as follows: 50 mg/mL exendin-4, 30 mM sodium acetate buffer pH 4-4.5, and 50 mg/mL of sucrose or mannitol. The polymer phase consisted of a 3A or 4A (50:50, lactide:glycolide) PLG as described above. The nominal load of exendin-4 for IF-1 through IF-4 was 1% w/w with a nominal load of sugar (mannitol or sucrose) at 1% w/w.

The release profiles for Initial Formulations 1-4 of Table 1 are depicted in FIG. 1.

Initial Formulation Development

Development of the Initial Formulations IF-1-IF-4 in Table 1 was based on achieving low initial release of exendin-4 coupled with sustained plasma levels of exendin-4. As such, the effects of various formulation and process parameters were examined. The parameters investigated included: encapsulation process, drug loading, polymer characteristics, drug formulation and excipients.

Polymer

The polymers employed in the development of the Initial Formulations are found in the list of polymers described above and were chosen to provide a release from about 3 weeks to about 3 months. As can be seen in Table 1, the Initial Formulations employed a 3A (50:50) and 4A (50:50) PLG. The Initial Formulations were found to release exendin-4 for about 3-4 weeks following administration.

Drug Loading

The drug loading in the formulations employed in the development of the Initial Formulations ranged from about 1% to about 5%. The drug loading refers to the nominal drug load and is a % (w/w) based on the final weight of the sustained release composition. For exendin-4, the high potency is amenable to drug loading in this range. As can be seen in Table 1 drug loading for the Initial Formulations was set at 1%.

Formulation of Drug

The majority of the development work resulting in the Initial Formulations was conducted with the exendin-4 in aqueous solutions. The solutions ranged in concentration from about 10 to 150 mg of exendin-4 per mL of water.

TABLE 1

| INITIAL FORMULATION | DRUG PHASE (INNER AQUEOUS EMULSION) | POLYMER PHASE | % EXENDIN-4 IN FORMULATION (W/W*, NOMINAL) | % EXCIPIENT IN FORMULATION (W/W, NOMINAL) |
|---|---|---|---|---|
| IF-1 | 50 mg/mL Exendin-4 50 mg/mL sucrose 30 mM sodium acetate (pH 4-4.5) | 3A 50:50 | 1% | 1% Sucrose |
| IF-2 | 50 mg/mL Exendin-4 50 mg/mL sucrose 30 mM sodium acetate (pH 4-4.5) | 4A 50:50 | 1% | 1% Sucrose |
| IF-3 | 50 mg/mL Exendin-4 50 mg/mL mannitol 30 mM sodium acetate (pH 4-4.5) | 3A 50:50 | 1% | 1% Mannitol |
| IF-4 | 50 mg/mL Exendin-4 50 mg/mL mannitol 30 mM sodium acetate (pH 4-4.5) | 4A 50:50 | 1% | 1% Mannitol |

*% W/W IS BASED ON THE FINAL WEIGHT OF THE COMPOSTION

Initially, exendin-4 was encapsulated from an aqueous solution alone (no excipients). Bioavailability of these formulations was variable however leading to studies aimed at determining potential stabilizing excipient for exendin-4. Exendin-4 stability was determined as a function of pH and concentration. As a result, formulations were prepared using acetate buffered solution at pH 4. Details of this study are set forth below in Example 1.

Formulations containing sucrose, ammonium sulfate or Tween –20 in the aqueous phase were also evaluated. Details of this study are set forth in Example 2.

Example 1

Effect of pH and Concentration on the Integrity of Unencapsulated Exendin-4 (pH 7)

Figure 2B:
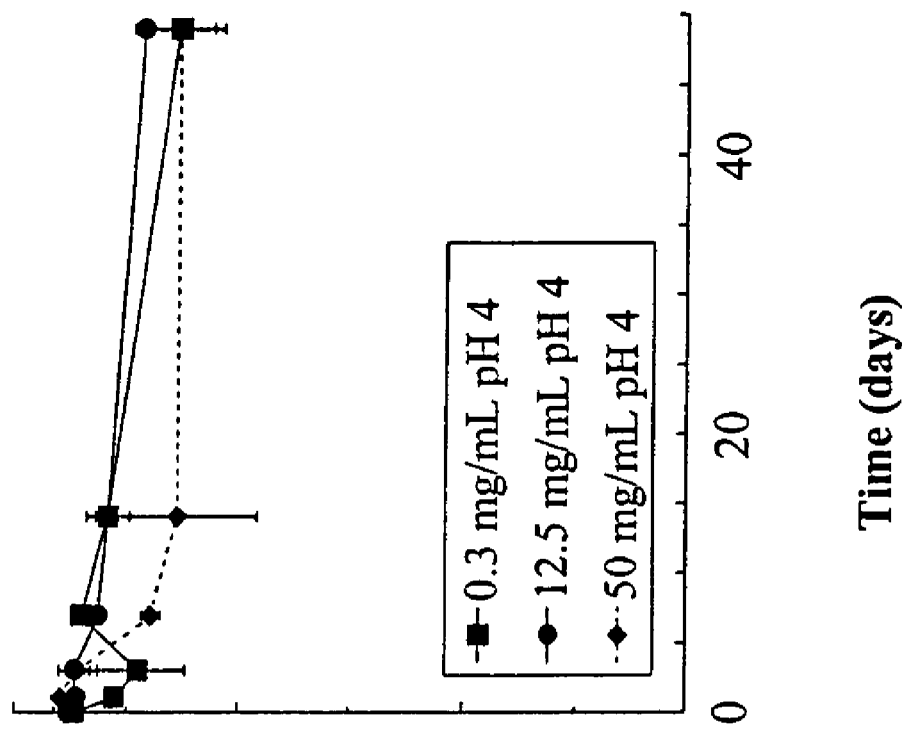
FIG. 2B is a graph of % Native Exendin-4 versus time in days for the described stability studies.
Figure 2A:
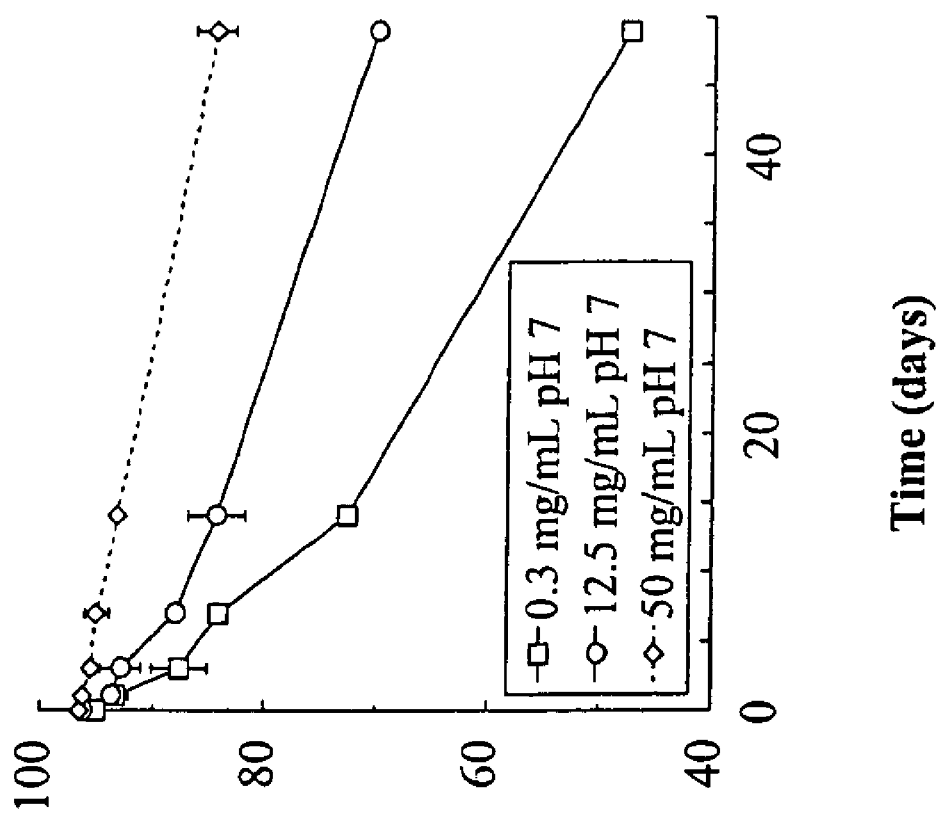
FIG. 2A is a graph of % Native Exendin-4 versus time in days for the described stability studies.

The effect of pH and concentration on the integrity of exendin-4 was investigated. The studies were conducted at 37° C. At pH 7 there was a dramatic loss of % native exendin-4 at the lowest concentration tested (0.3 mg/mL). The rate of loss was decreased as the concentration was increased to 12.5 mg/mL and at 50 mg/mL stability was further improved. The results are depicted graphically in FIG. 2A.

Example 2

Effect of pH and Concentration on the Integrity of Unencapsulated Exendin-4 (pH 4)

The same series of exendin-4 concentrations as described in Example 1 were conducted at pH 4. Good stability was observed over the entire concentration range up to 49 days of incubation. The results of testing at pH 4 are set forth in FIG. 2B.

Example 3

Effect of Excipients on the Integrity of Unencapsulated Exendin-4

The effect of adding various excipients to exendin-4 formulated at 50 mg/mL and pH 4 was examined. The excipients tested were sucrose and ammonium sulfate, both at at a 1:1 weight ratio with the exendin-4 (i.e., 50 mg/mL) and 0.1% TWEEN-20.

Figure 3:
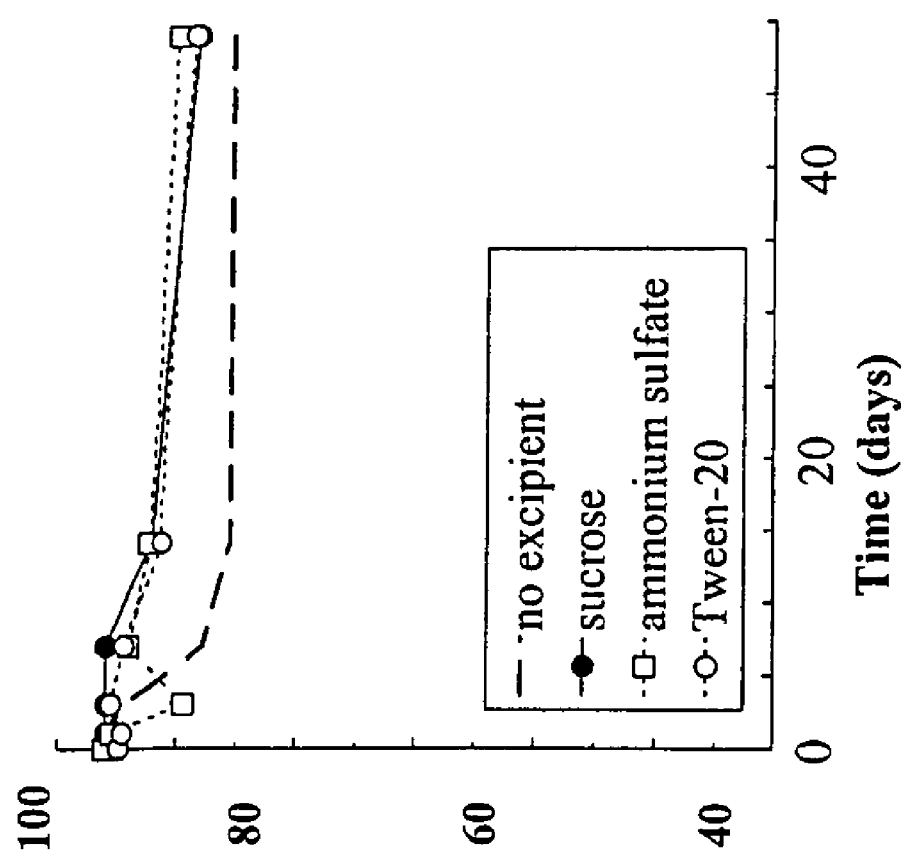
FIG. 3 is a graph of % Native Exendin-4 versus time in days for the described stability studies.

As can be seen in FIG. 3. there was further moderate improvement in exendin-4 stability in the presence of the excipients.

Example 4

Microparticle Development

A series of microparticle batches were prepared using the W/O/O process described above. A description of each microparticle formulation is set forth in Table 2. Briefly, the effect of exendin-4 concentration in the inner aqueous phase (12.5 mg/mL or "high water" and 50 mg/mL or "low water") and the addition of sucrose or ammonium sulfate (at an equal weight relative to exendin) to the inner aqueous phase was examined. In all cases the inner aqueous phase contained 30 mM acetate buffer at pH 4.

TABLE 2

| MICRO-PARTICLE LOT | % EXENDIN-4 IN FORMULATION (W/W) | % EXCIPIENT IN FORMULATION (W/W) | POLYMER | DRUG PHASE | Cmax (pg/mL) | BIO-AVAILABILITY (%) |
|---|---|---|---|---|---|---|
| M-1 | 1% | 0% | 4A | 50 mg/mL, pH = 4 | 383 ± 240 | 8 |
| M-2 | 1% | 0% | 4A | 12.5 mg/mL pH = 4 | 855 ± 127 | 4 |
| M-3 | 1% | 1% SUCROSE | 4A | 50 mg/mL, pH = 4, sucrose | 1366 ± 1860 | 15 |
| M-4 | 1% | 1% SUCROSE | 4A | 12.5 mg/mL, pH = 4, sucrose | 988 ± 170 | 10 |
| M-5 | 1% | 1% AMMONIUM SULFATE | 4A | 50 mg/mL, pH = 4, $(NH_4)_2SO_4$ | 15371 ± 8597 | 45 |
| M-6 | 1% | 1% AMMONIUM SULFATE | 4A | 12.5 mg/mL, pH = 4, $(NH_4)_2SO_4$ | 10839 ± 875 | 60 |

Figure 4:
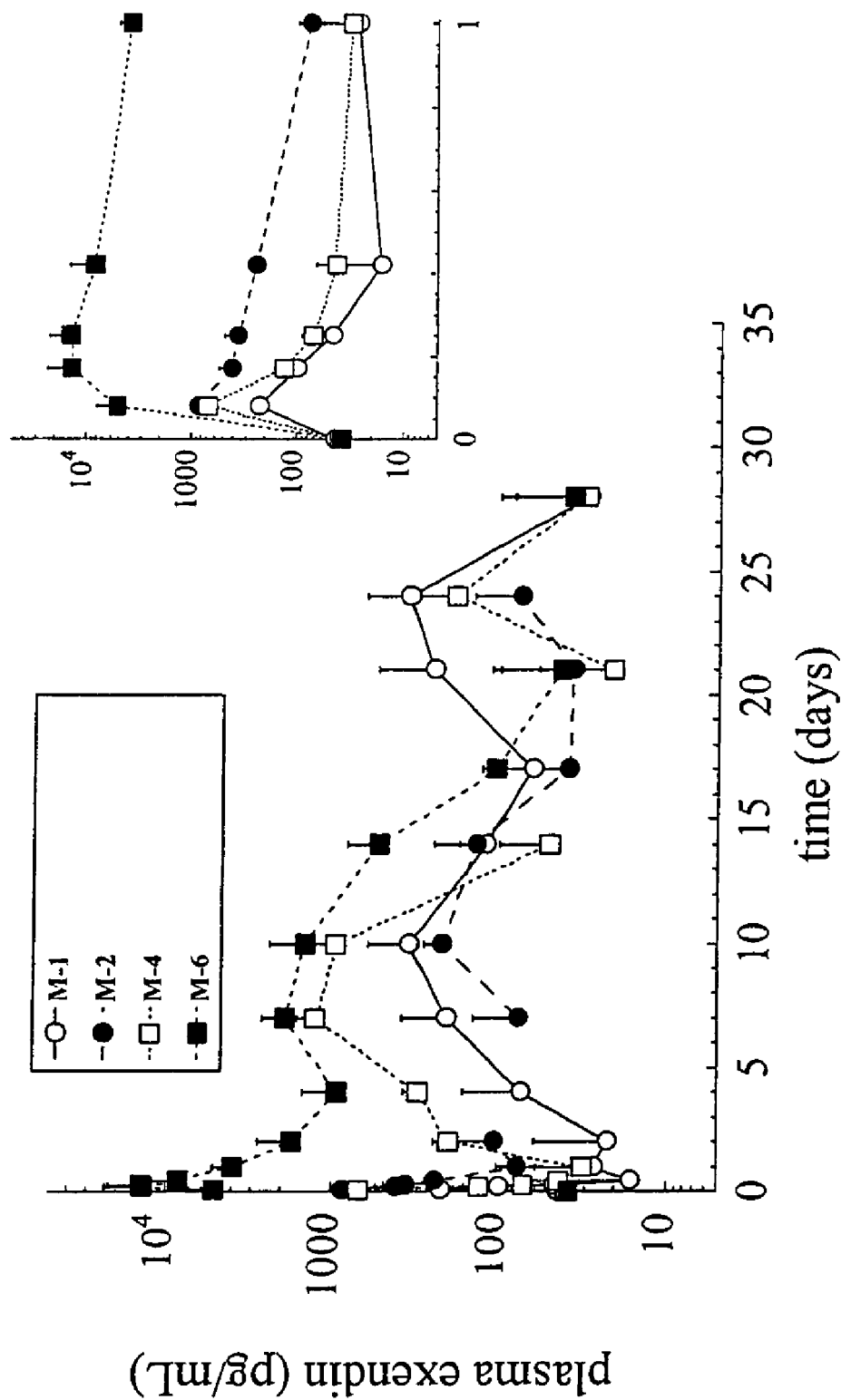
FIG. 4 is a graph of plasma levels (pg/mL) in rats of exendin-4 versus time in days post administration for the selected microparticle formulations.

The release profiles for Formulations M-1, M-2, M-4 and M-6 are set forth in FIG. 4. The release profile shows that the low water formulation had a lower Cmax, the addition of sucrose resulted in a less pronounced lag phase following the initial release and generally higher levels of exendin-4 for about the first two weeks, and the ammonium sulfate-containing batch exhibited a large initial release.

Example 5

Additional Microparticle Formulations

Additional microparticles formulations were prepared in developing the Initial Formulations. All of the microparticle formulations were prepared using a W/O/O process. Polymer type was either 3A or 4A PLG 50:50 described above. The load of exendin-4, sucrose and water were varied. In addition, mannitol as an excipient was investigated. A description of each microparticle formulation is set forth in Table 3.

TABLE 3

| MICRO-PARTICLE LOT | % EXENDIN-4 IN FORMULATION (W/W) | % EXCIPIENT IN FORMULATION (W/W) | POLYMER PHASE | DRUG PHASE | Cmax (pg/mL) | BIO-AVAILABILITY (%) |
|---|---|---|---|---|---|---|
| M-7 | 1% | 1% SUCROSE | 4A | 50 mg/mL, pH = 4, sucrose | 1482 ± 640 | 18 |
| M-8 | 1% | 1% SUCROSE | 3A | 50 mg/mL, pH = 4, sucrose | 1794 ± 615 | 27 |
| M-9 | 1% | 2% SUCROSE | 4A 0.2% $MgCO_3$ | 50 mg/mL, pH = 4, sucrose | 1087 ± 178 | 13 |
| M-10 | 1% | 2% SUCROSE | 4A | M-7 with 2X sucrose | 2607 ± 911 | 29 |
| M-11 | 2% | 2% SUCROSE | 4A | M-7 with 2X sucrose, exendin-4 and water | 1658 ± 522 | 18 |
| M-12 | 2% | 2% SUCROSE | 4A | M-7 with 2X sucrose and exendin-4 (100 mg/mL) | 7691 ± 229 | 26 |
| M-13 | 1% | 1% MANNITOL | 4A | M-7 with mannitol in place of sucrose | 1115 ± 687 | 18 |
| M-14 | 1% | 1% MANNITOL | 3A | M-7 with mannitol in place of sucrose | 1884 ± 820 | 22 |

Figure 5:
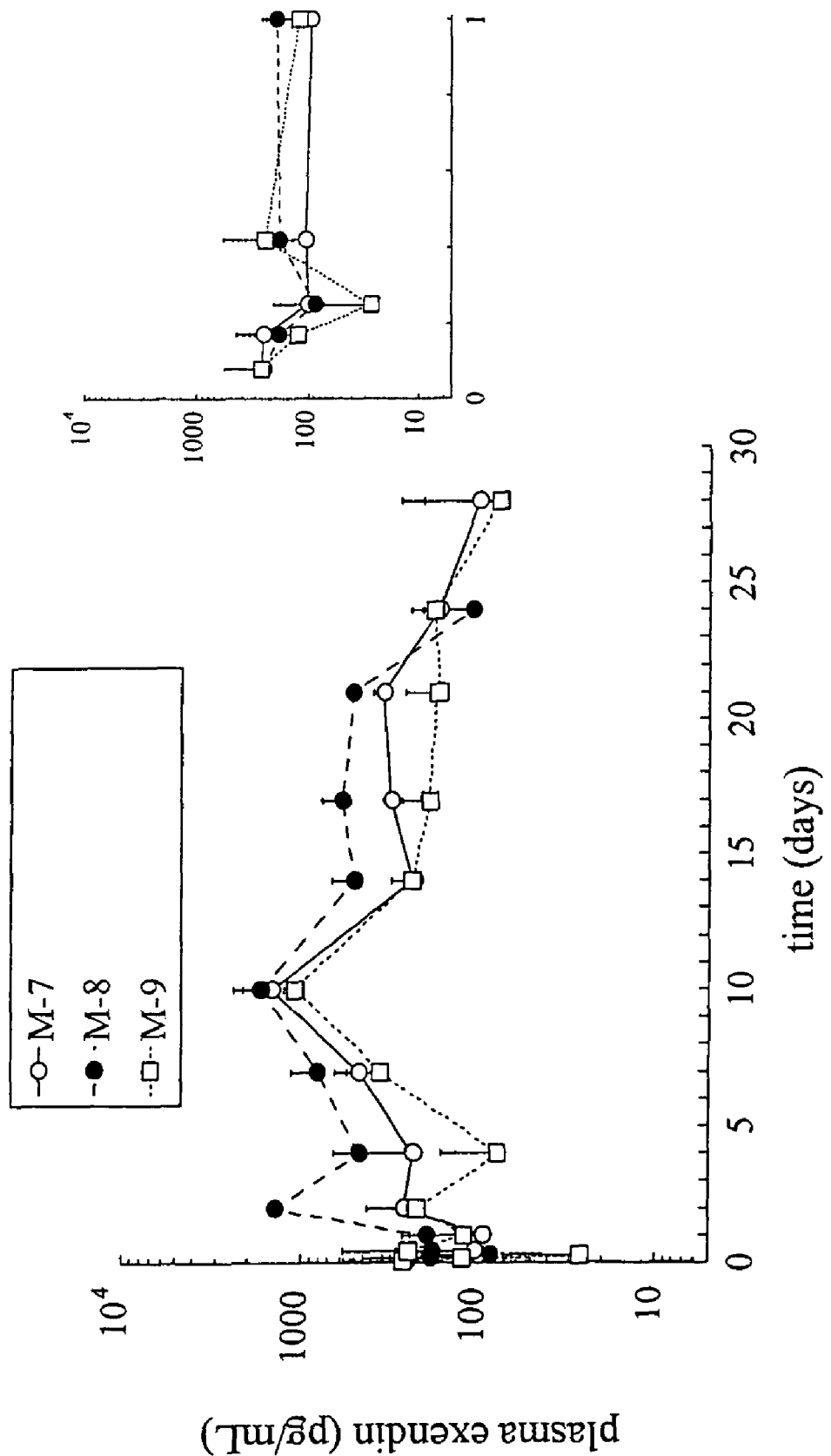
FIG. 5 is a graph of plasma levels (pg/mL) in rats of exendin-4 versus time in days post administration for the selected microparticle formulations.
Figure 6:
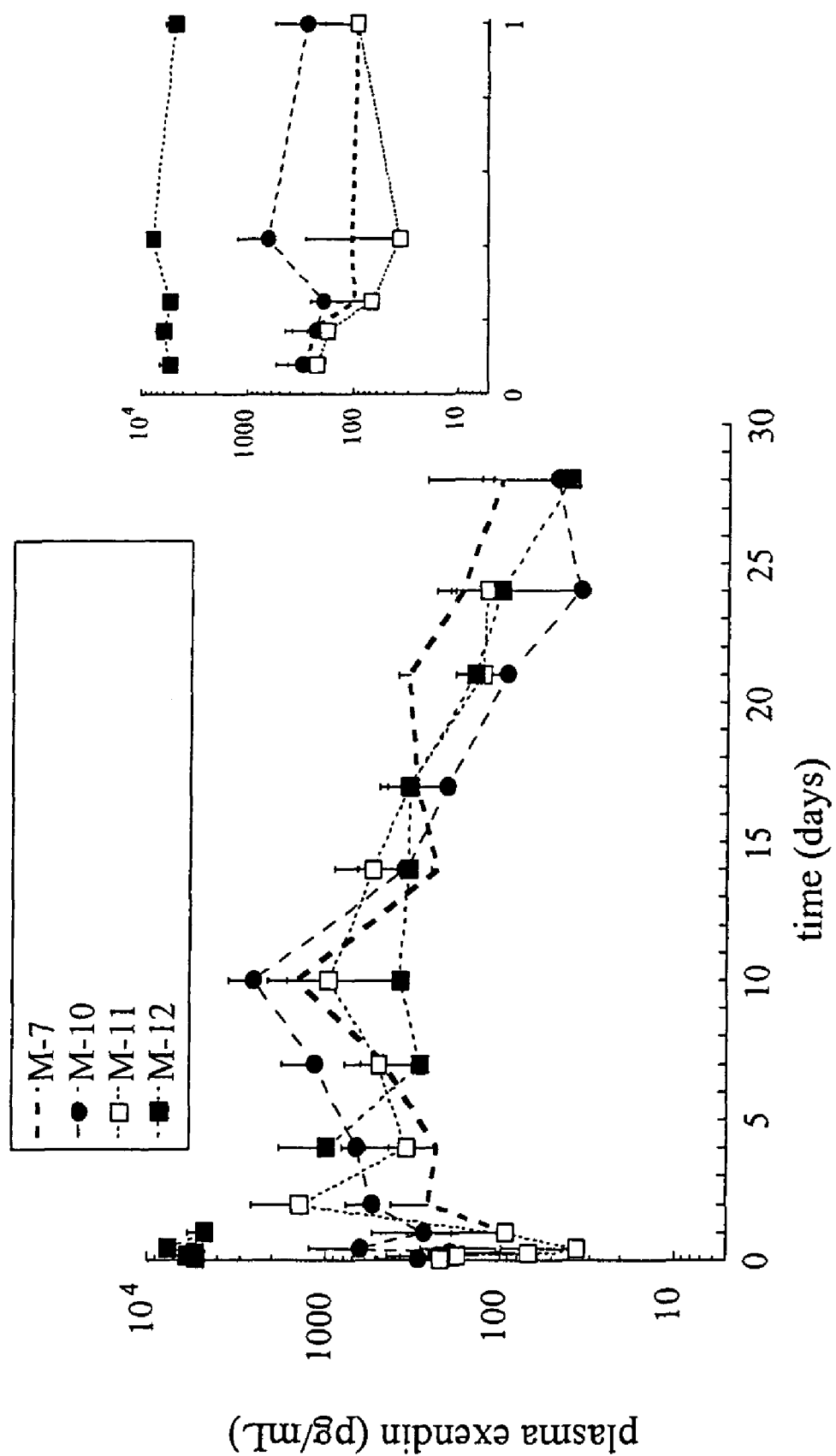
FIG. 6 is a graph of plasma levels (pg/mL) in rats of exendin-4 versus time in days post administration for the selected microparticle formulations.
Figure 7:
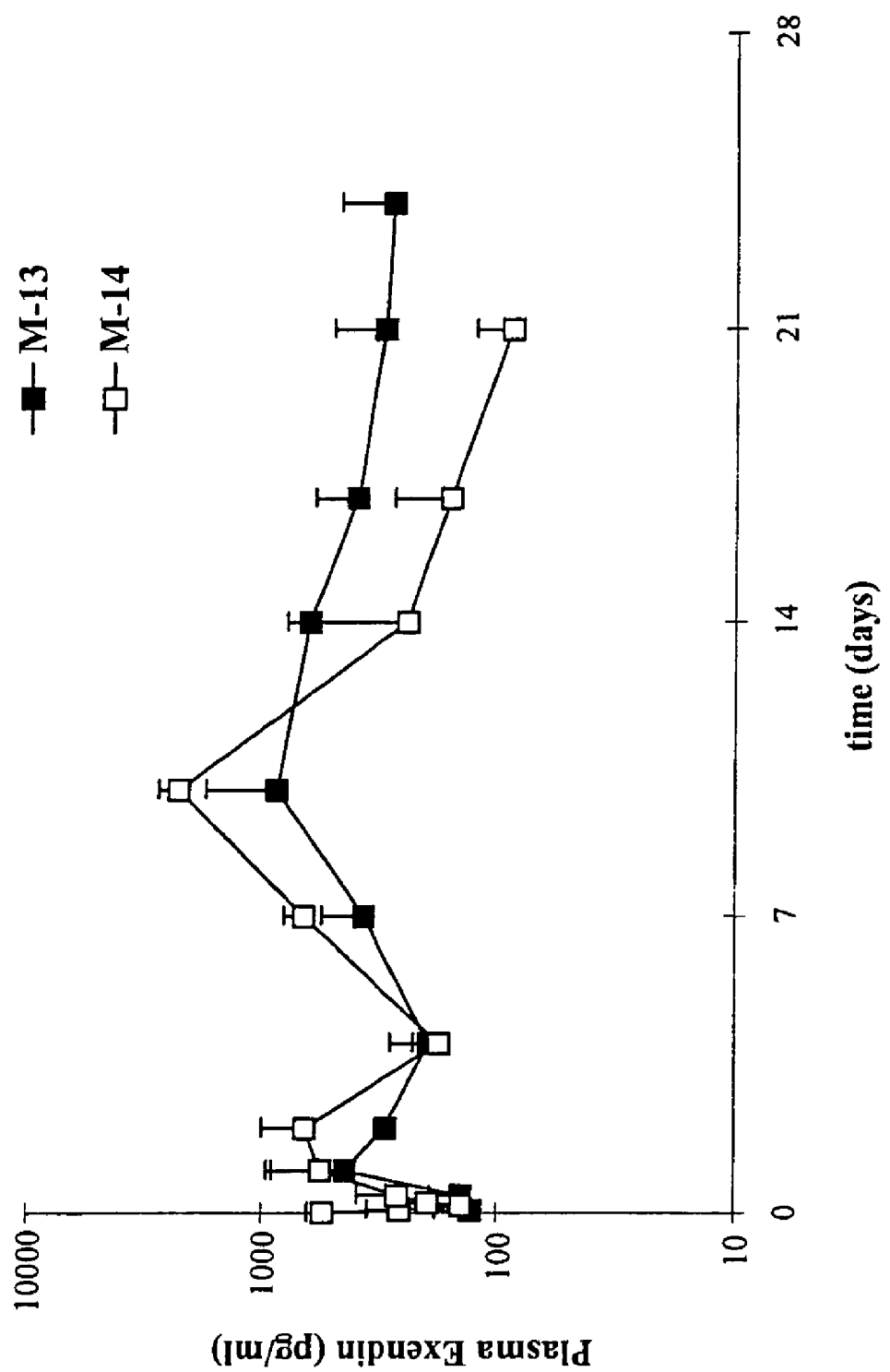
FIG. 7 is a graph of plasma levels (pg/mL) in rats of exendin-4 versus time in days post administration for the selected microparticle formulations.

The release profiles for Microparticle Formulations M-7, M-8 and M-9 are depicted graphically in FIG. 5. The release profiles for Microparticle Formulations M-7, M10, M-11 and M-12 are depicted graphically in FIG. 6. The release profile of Microparticle Formulations M-13 and M-14 are depicted graphically in FIG. 7.

Initial Formulations—In Vivo

Figure 8:
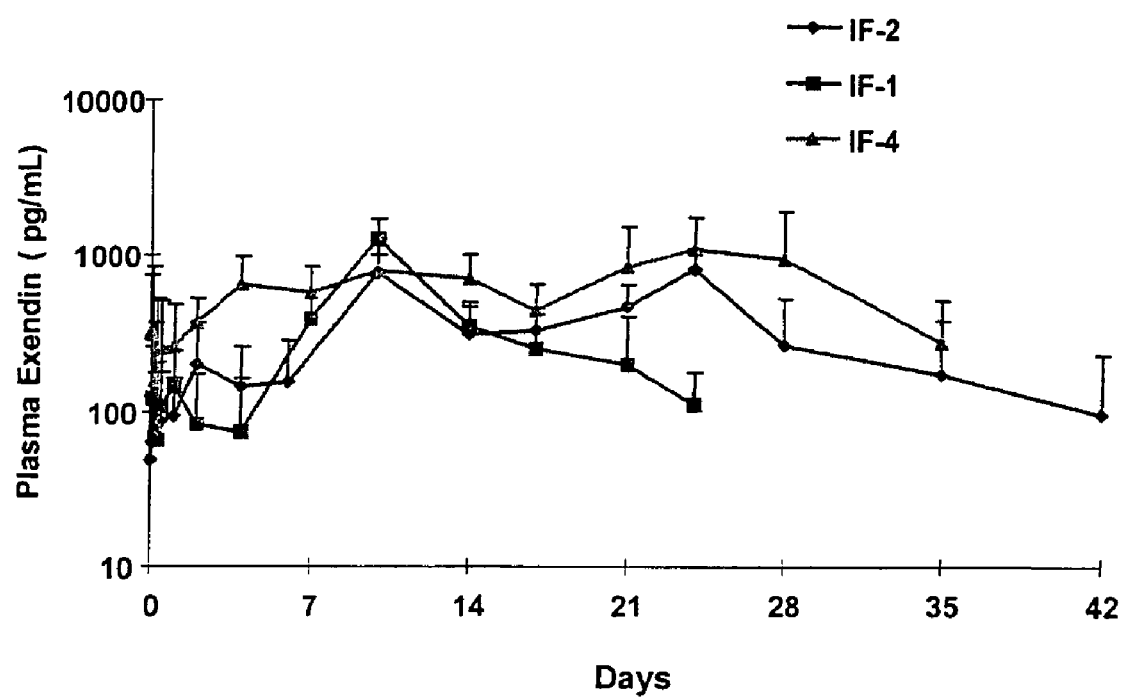
FIG. 8 is a graph of plasma levels (pg/mL) for formulations, IF-1, -2 and -4 in Rats versus time in days post administration.

The Initial Formulations, IF-1, -2 and -4 of Table 1 were then administered to rats. The release profiles for these formulations are depicted in FIG. 1 through 28 days post administration and in FIG. 8 through 42 days post administration. Inspection of FIG. 8 shows that IF-1, -2 and -4 provided an acceptable release profile in rats (15-32% bioavailability with a Cmax/Cave of about 2-3). Further research to discover formulations with additional improvements in the release profile of exendin-4 was then conducted resulting in the Selected Formulations (SF) described below.

Such further formulation discovery was directed at increasing drug load and determining excipients capable of further increasing bioavailability. Loads were examined in the range of 1% to 4%. Various excipients were tested including ammonium sulfate, acetate buffer, sugars, such as sucrose, mannitol and trehalose and the surfactant, Pluronic F-127.

Selected Formulations

The Selected Formulations resulting from the further formulation discovery, which were chosen for clinical testing, are set forth in Table 4.

TABLE 4

| SELECTED FORMULATION | % EXENDIN-4 IN FORMULATION W/W NOMINAL (W/W ACTUAL) | % EXCIPIENT IN FORMULATION W/W | DRUG PHASE (INNER AQUEOUS EMULSION) | POLYMER PHASE |
|---|---|---|---|---|
| SF-1 | 3% (2.5%) | 2% SUCROSE, 0.3% AMMONIUM SULFATE | Exendin-4 (50 mg/mL in water) 2% sucrose, 0.3% ammonium sulfate | 4A 50:50 |

TABLE 4-continued

| SELECTED FORMULATION | % EXENDIN-4 IN FORMULATION W/W NOMINAL (W/W ACTUAL) | % EXCIPIENT IN FORMULATION W/W | DRUG PHASE (INNER AQUEOUS EMULSION) | POLYMER PHASE |
|---|---|---|---|---|
| SF-2 | 3% (2.8%) | 2% SUCROSE, 0.5% AMMONIUM SULFATE | Exendin-4 (50 mg/mL in water) 2% sucrose, 0.5% ammonium sulfate | 4A 50:50 |

Figure 9:
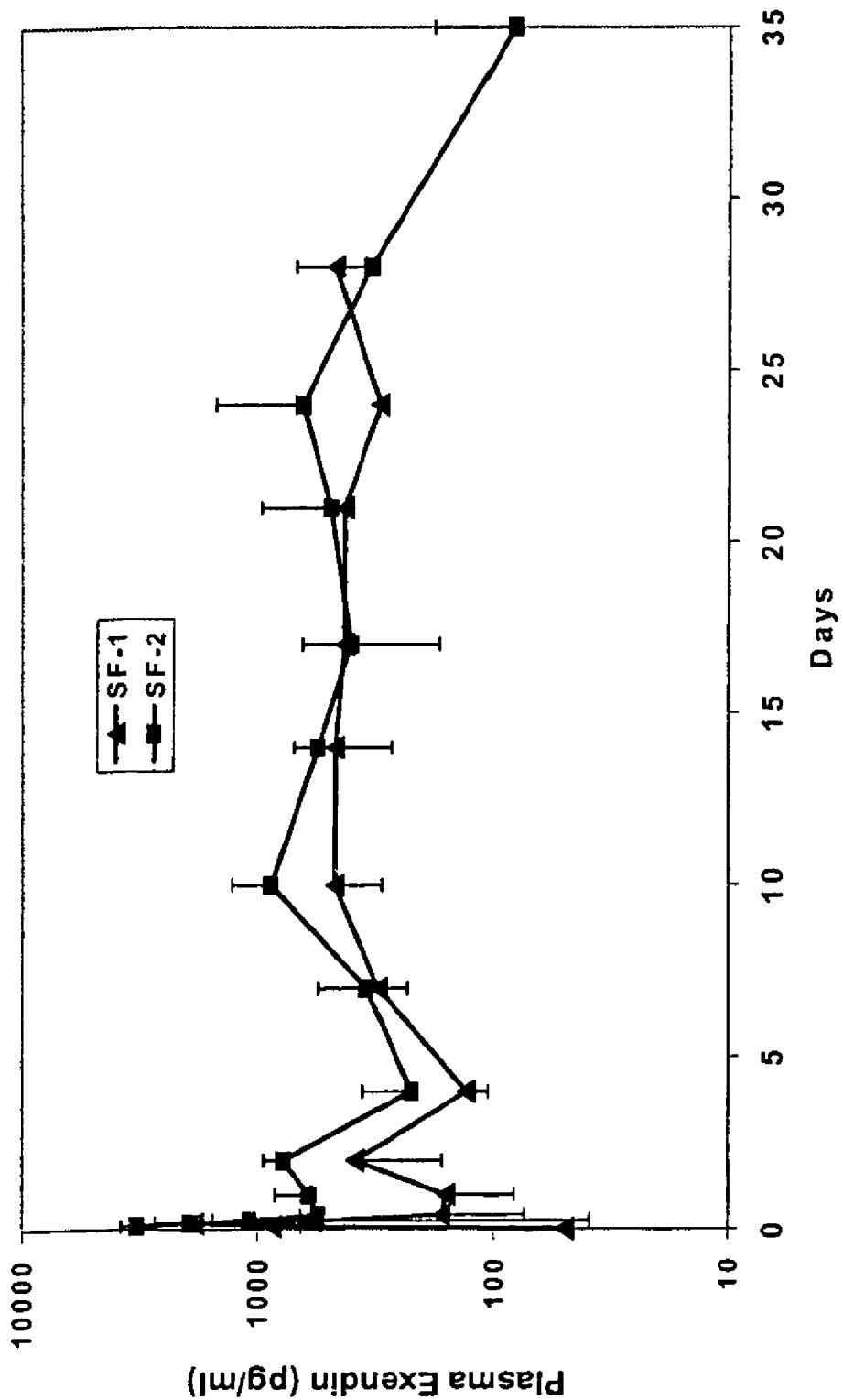
FIG. 9 is a graph of plasma levels (pg/mL) in rats of exendin-4 versus time in days post administration for formulations SF-1 and SF-2.

The sustained release profiles in rats for SF-1 (3% drug, 2% sucrose, 0.3% AS) and SF-2 (3% drug, 2% sucrose, 0.5% AS) are depicted graphically in FIG. 9.

Additional Formulation Discovery

Figure 11:
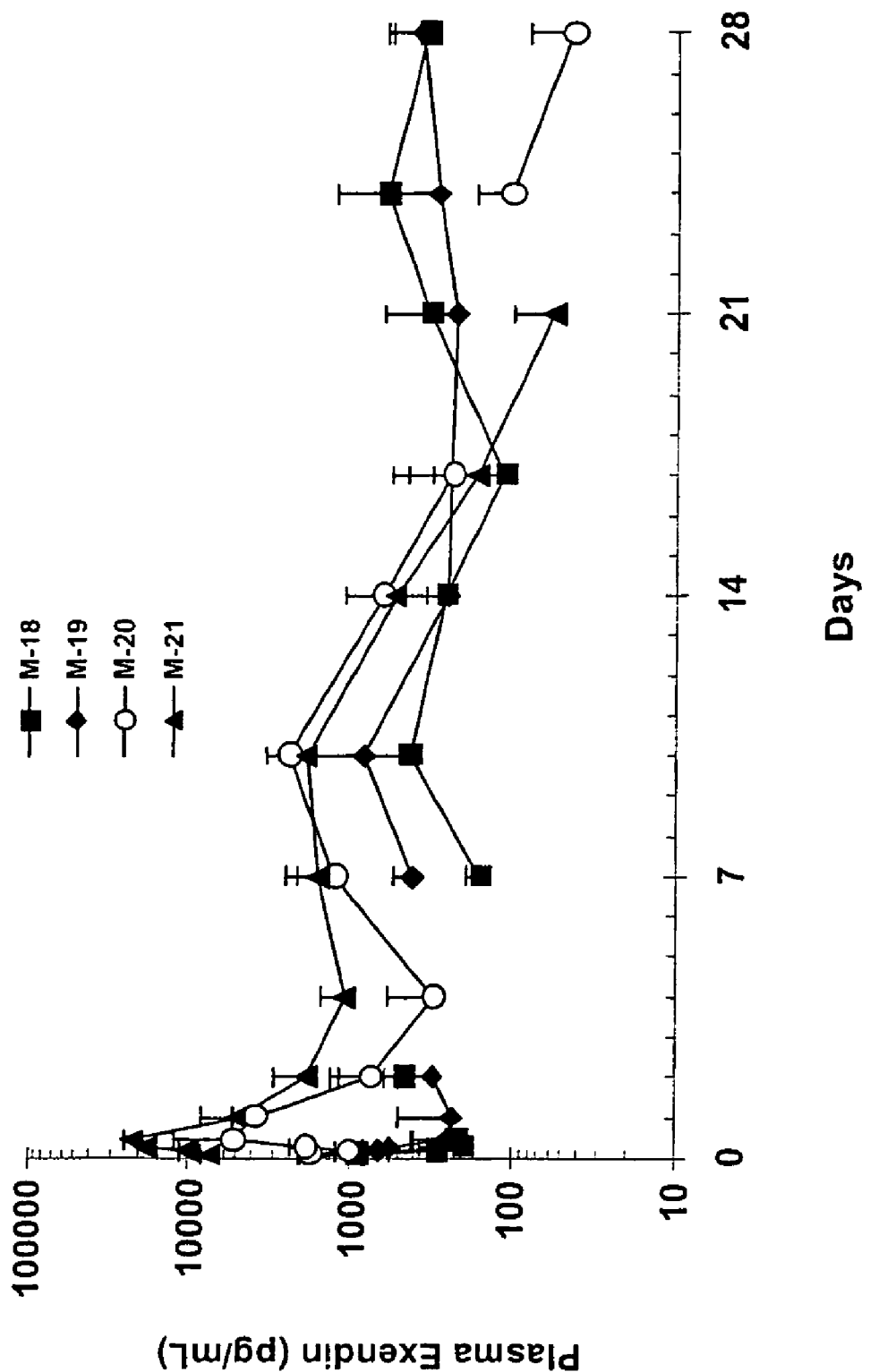
FIG. 11 is a graph of plasma levels (pg/mL) in rats of exendin-4 versus time in days post administration for the selected microparticle formulations.

% LOAD VARIATION: Previously a 1% loading had been employed (Initial Formulations 1-4). Higher loads were tested to determine a range of drug loading for exendin-4. It was found that increasing the load from 1% to the range of about 2-3% was acceptable. Loads of 4% and higher for exendin-4 resulted in an increased Cmax. The Microparticle AMMONIUM SULFATE: The effect of ammonium sulfate on the release of exendin from microparticle formulations was further investigated. FIG. 11 shows that addition of 0.5% ammonium sulfate generally increases exendin-4 plasma levels over the first two weeks. There was a dramatic increase in bioavailability from about 12-15% to about 38-57%. However there was also an undesirable increase in the Cmax when ammonium sulfate was used alone. The Microparticle Formulations depicted in FIG. 11 are set forth in Table 5.

TABLE 5

| MICRO-PARTICLE LOT | % EXENDIN-4 IN FORMULATION W/W NOMINAL (W/W ACTUAL) | % EXCIPIENT IN FORMULATION W/W | DRUG PHASE (INNER AQUEOUS EMULSION) | POLYMER PHASE |
|---|---|---|---|---|
| M-18 | 2% (1.89%#, 1.98%*) | 2% MANNITOL | Exendin-4 (50 mg/mL in 80 mM acetate buffer, pH = 4.0) 2% mannitol | 4A 50:50 |
| M-19 | 2% (1.79%*, 1.80%#) | 2% MANNITOL | Exendin-4 (50 mg/mL in 80 mM acetate buffer, pH = 4.0) 2% mannitol | 4A 50:50 |
| M-20 | 2% (1.73%*, 1.74%#) | 2% MANNITOL 0.5% AMMONIUM SULFATE | Exendin-4 (50 mg/mL in 80 mM acetate buffer, pH = 4.0) 2% mannitol, 0.5% ammonium sulfate | 4A 50:50 |
| M-21 | 2% (1.72%*, 1.75%#) | 2% MANNITOL 0.5% AMMONIUM SULFATE | Exendin-4 (50 mg/mL in 80 mM acetate buffer, pH = 4.0) 2% mannitol, 0.5% ammonium sulfate | 4A 50:50 |

SE METHOD
*NITROGEN METHOD

Figure 10:
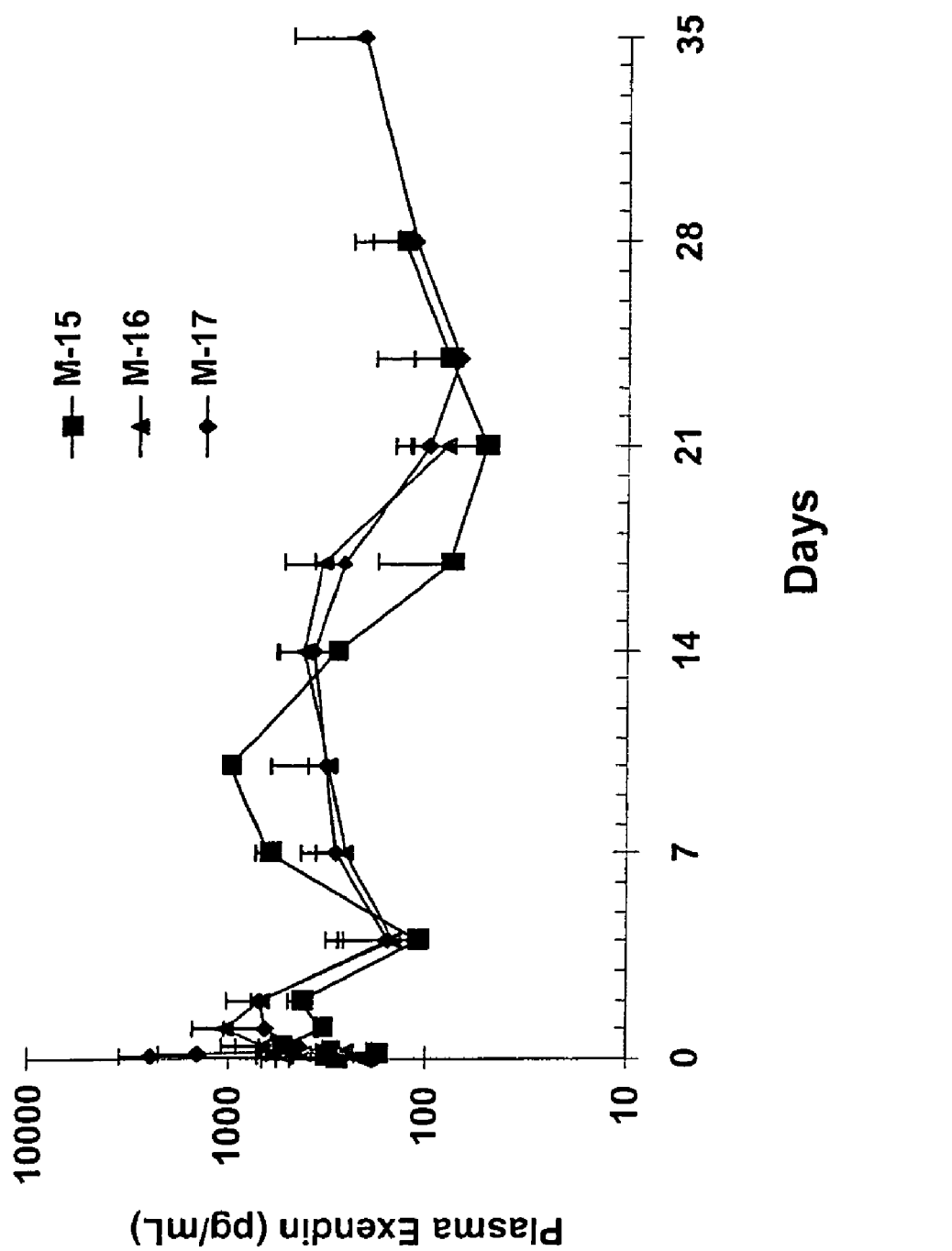
FIG. 10 is a graph of plasma levels (pg/mL) in rats of exendin-4 versus time in days post administration for the selected microparticle formulations.

Formulations M15-M17 are described below and the sustained release profile for each is depicted graphically in FIG. 10.

M-15-M-17:
All microparticles contained 1:1 mannitol:drug (w:w) and 80 mM acetate buffer (pH=4.0) encapsulated in 4A, 50:50 PLG
M-15: 2% load
M-16: 3% load
M-17: 4% load SUGAR EXCIPIENT: Earlier formulations used sucrose and mannitol as the sugar excipient at a 1% load in the microparticle or a 1:1 sugar:exendin-4 (w:w). In this further formulation development, sucrose, mannitol and trehalose, all at 2% load, were evaluated. In this study, the drug load was also 2% (therefore sugar-to-drug ratio remained 1%) and the microparticles also had 0.5% ammonium sulfate present.

Figure 12:
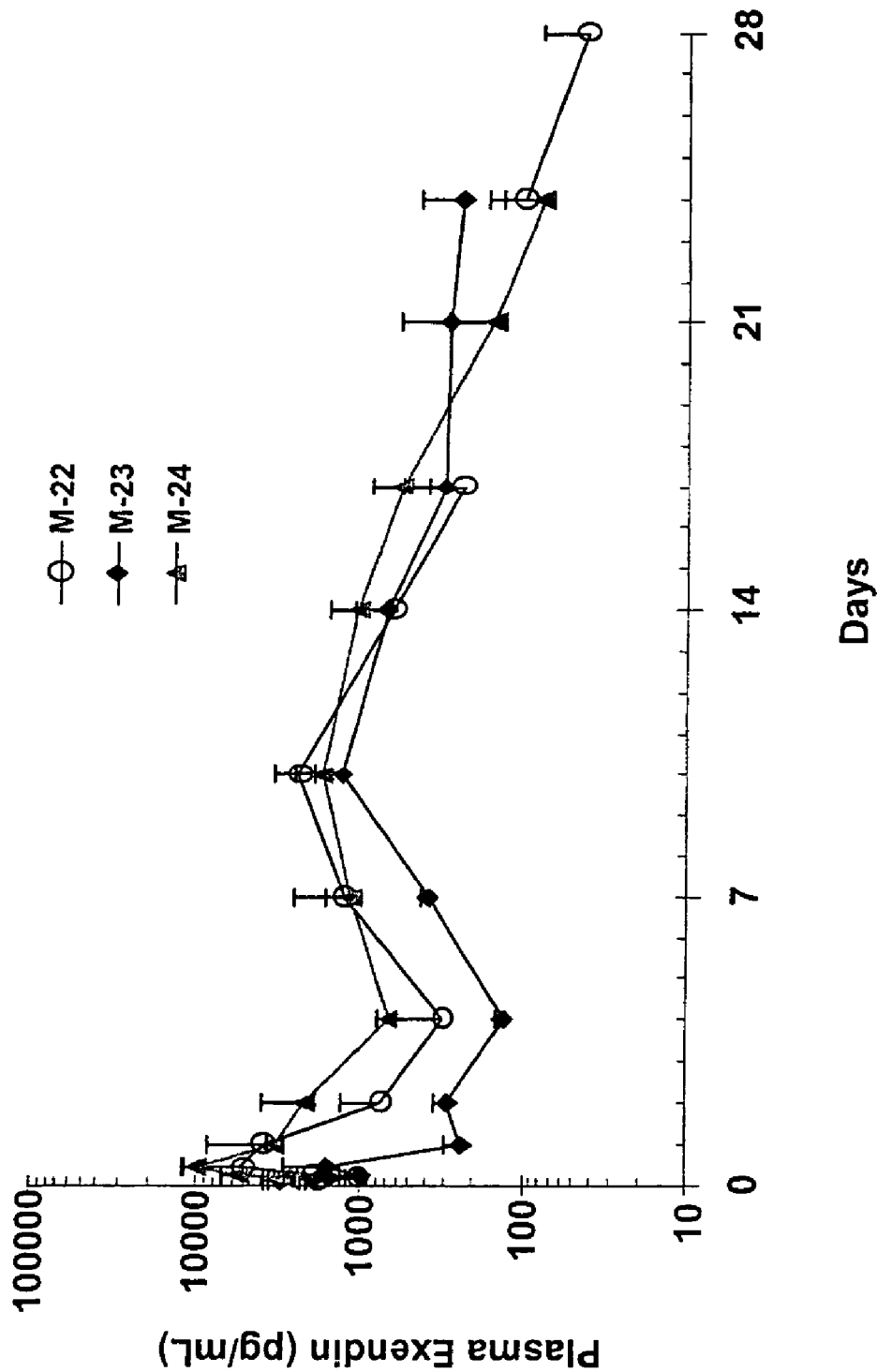
FIG. 12 is a graph of plasma levels (pg/mL) in rats of exendin-4 versus time in days post administration for the selected microparticle formulations.
Figure 13:
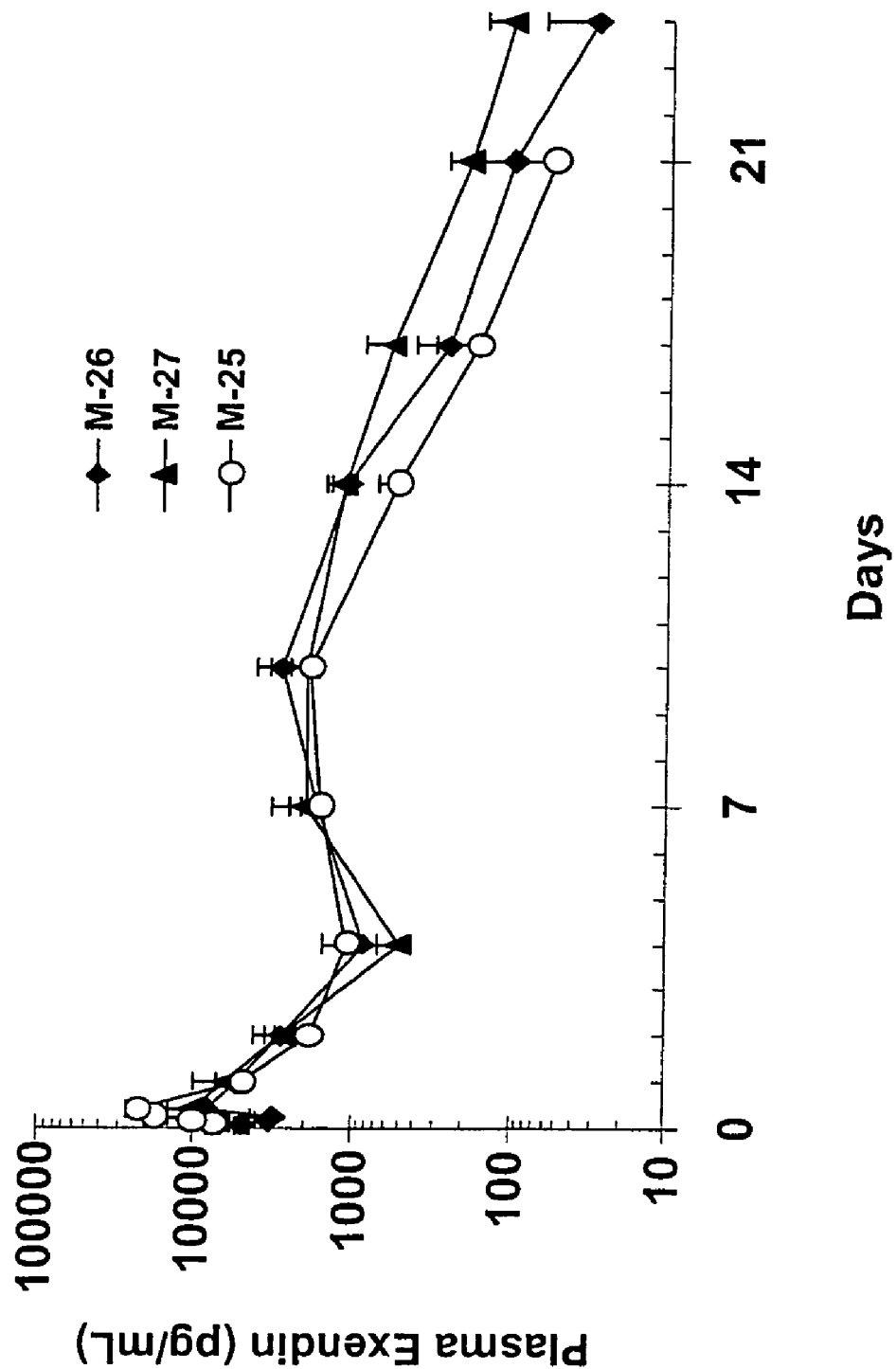
FIG. 13 is a graph of plasma levels (pg/mL) in rats of exendin-4 versus time in days post administration for the selected microparticle formulations.
Figure 14:
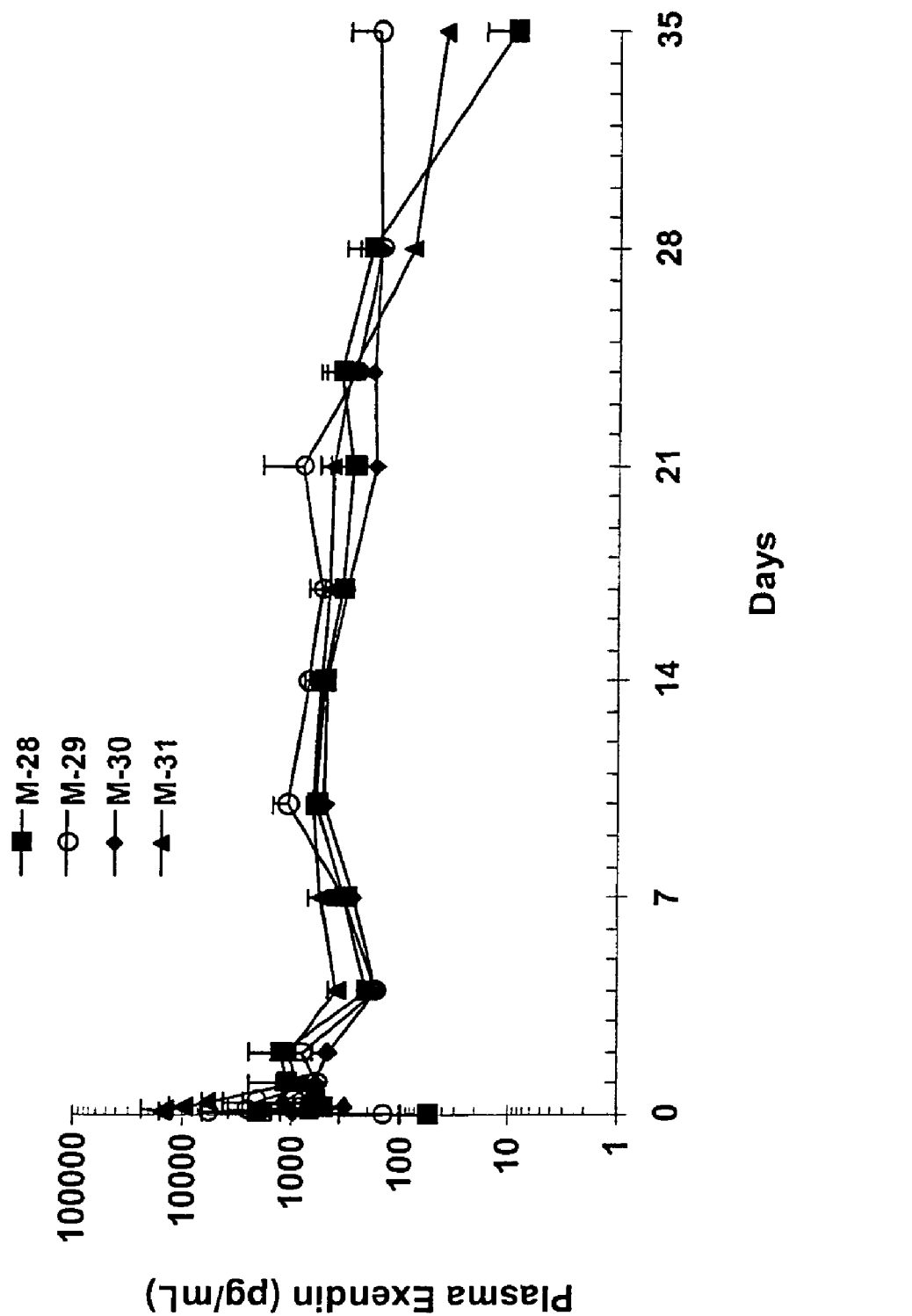
FIG. 14 is a graph of plasma levels (pg/mL) in rats of exendin-4 versus time in days post administration for the selected microparticle formulations.
Figure 15:
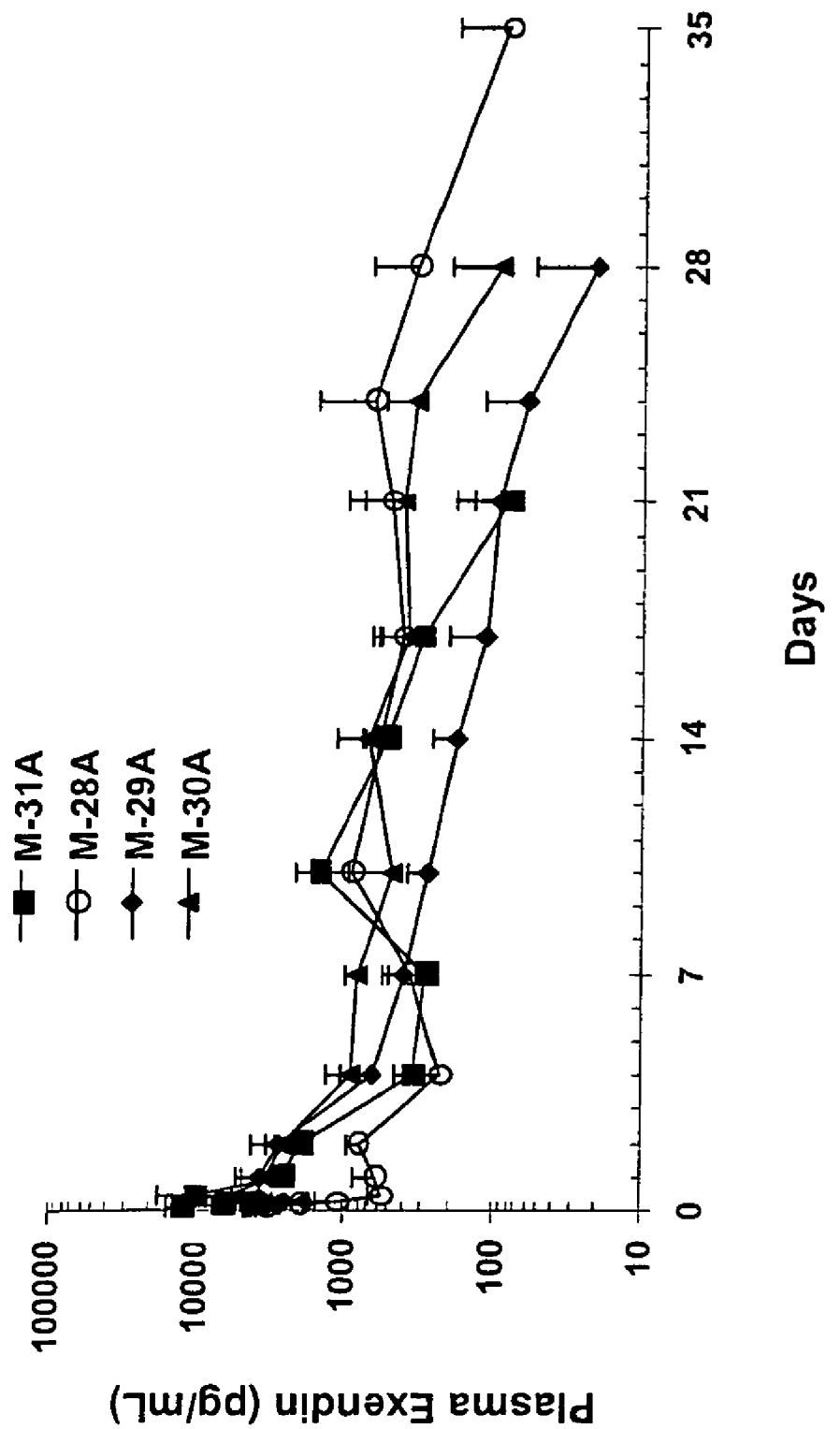
FIG. 15 is a graph of plasma levels (pg/mL) in rats of exendin-4 versus time in days post administration for the selected microparticle formulations.
Figure 16:
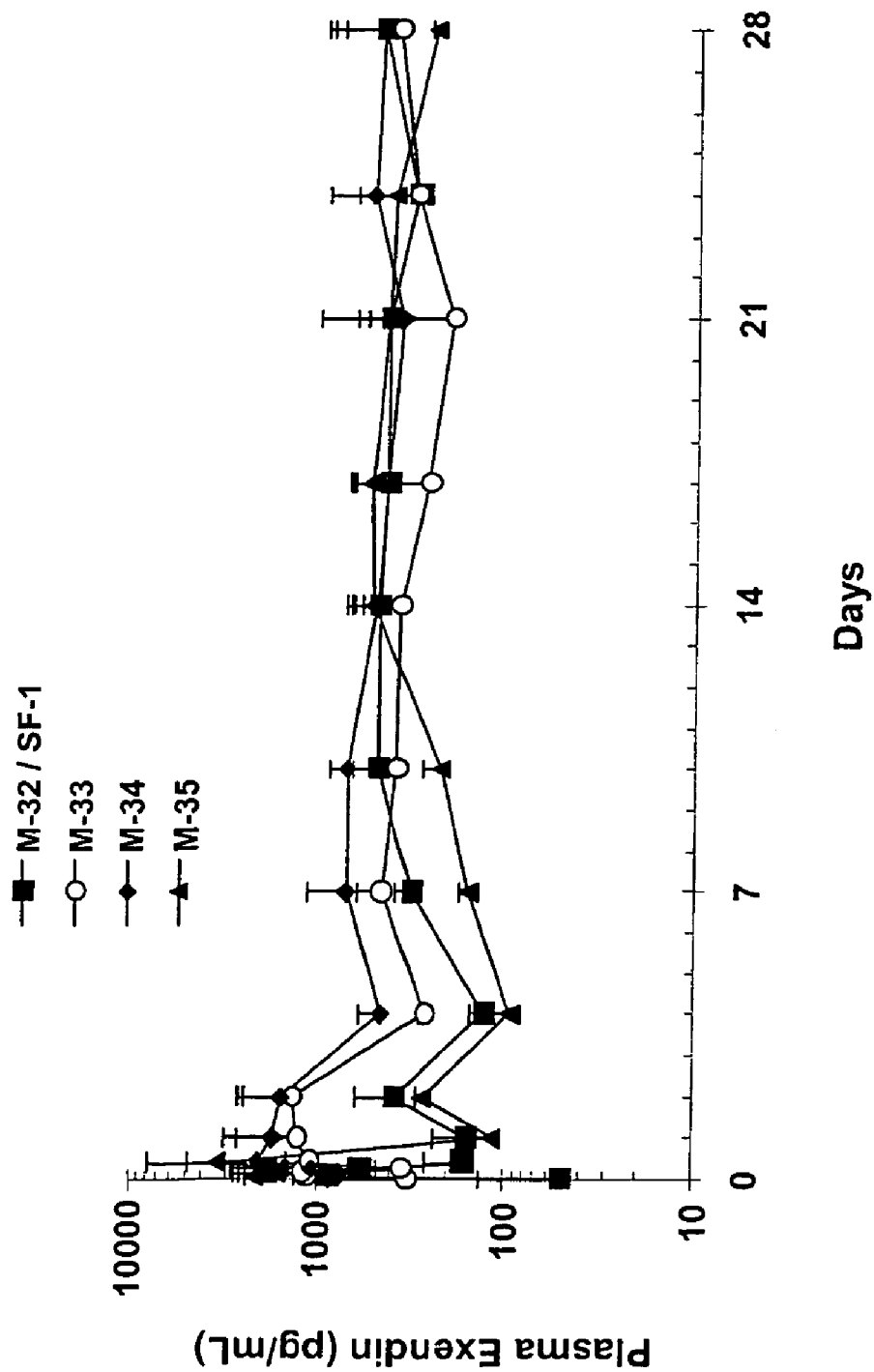
FIG. 16 is a graph of plasma levels (pg/mL) in rats of exendin-4 versus time in days post administration for the selected microparticle formulations.

The sustained release profile for these formulation is set forth in FIG. 12. The Microparticle Formulations are as shown in Table 6.

TABLE 6

| MICRO-PARTICLE LOT | % EXENDIN-4 IN FORMULATION W/W NOMINAL (W/W ACTUAL) | % EXCIPIENT IN FORMULATION W/W | DRUG PHASE (INNER AQUEOUS EMULSION) | POLYMER PHASE |
|---|---|---|---|---|
| M-22 | 2% (1.73%*, 1.74%#) | 2% MANNITOL 0.5% AMMONIUM SULFATE | Exendin-4 (50 mg/mL in 80 mM acetate buffer, pH = 4.0) 2% mannitol. 0.5% ammonium sulfate | 4A 50:50 |
| M-23 | 2% (1.66%*, 1.68%#) | 2% SUCROSE 0.5% AMMONIUM SULFATE | Exendin-4 (50 mg/mL in 80 mM acetate buffer, pH = 4.0) 2% sucrose, 0.5% ammonium sulfate | 4A 50:50 |
| M-24 | 2% (1.86%#, 1.90%*) | 2% TREHALOSE 0.5% AMMONIUM SULFATE | Exendin-4 (50 mg/mL in 80 mM acetate buffer, pH = 4.0) 2% trehalose, 0.5% ammonium sulfate | 4A 50:50 |

SE METHOD
*NITROGEN METHOD

The sustained release profiles in FIG. 12 show that mannitol and trehalose tend to provide a higher Cmax than sucrose and higher plasma levels over about the first week of release.

ACETATE BUFFER: The majority of formulations prepared included 80 mM sodium acetate buffer in the inner aqueous phase during microencapsulation. In this further formulation development, lower levels (30 mM) and also the absence of acetate buffer were evaluated. The release profile for Microparticle Formulations M-25-M-27 is depicted graphically in FIG. 13. Inspection of the sustained release profile of FIG. 13 suggest that the buffer can be removed from the formulation possibly resulting in a reduced Cmax and without impacting the drug integrity. The Microparticle Formulations M-25, M-26 and M-27 are set forth in Table 7.

DESIGN-OF-EXPERIMENTS (DOE) APPROACH: Based on the discovery work described above, a design-of-experiments approach was employed to select formulations. Briefly, buffer was removed from the formulations, sugar content was fixed at 2%. The variables which were examined were drug load (2 or 3%), sugar type (sucrose or mannitol) and level of ammonium sulfate (0.3 or 0.5%). The three variable, two-level design resulted in a total of 8 formulations from which the Selected Formulations, SF-1 and SF-2 were identified. The studies are set forth below.

DOE STUDY 1: Formulations containing 0.5% ammonium sulfate were evaluated. The sustained release profile for the formulations are set forth in FIG. 14. One of the batches (2% drug load with mannitol) was prepared at the 100 g scale

TABLE 7

| Microparticle Formulation Identifier | % EXENDIN-4 IN FORMULATION W/W NOMINAL (W/W ACTUAL) | % EXCIPIENT IN FORMULATION W/W | DRUG PHASE (INNER AQUEOUS EMULSION) | POLYMER PHASE |
|---|---|---|---|---|
| M-25 | 2% (1.72%*, 1.75%#) | 2% MANNITOL 0.5% AMMONIUM SULFATE | Exendin-4 (50 mg/mL in 80 mM acetate buffer, pH = 4.0) 2% mannitol. 0.5% ammonium sulfate | 4A 50:50 |
| M-26 | 2% (1.65%*, 1.68%#) | 2% MANNITOL 0.5% AMMONIUM SULFATE | Exendin-4 (50 mg/mL in WATER) 2% mannitol, 0.5% ammonium sulfate | 4A 50:50 |
| M-27 | 2% (1.71%*, 1.77%#) | 2% TREHALOSE 0.5% AMMONIUM SULFATE | Exendin-4 (50 mg/mL in 30 mM acetate buffer, pH = 4.0) 2% trehalose, 0.5% ammonium sulfate | 4A 50:50 |

SE METHOD
*NITROGEN METHOD and a precipitate was observed in the primary emulsion possibly resulting in the higher Cmax observed. The bioavailability was in the range of 15-30% for these formulations. A description of the Microparticle Formulations M-28-M-31 is set forth in Table 8.

TABLE 8

| MICRO-PARTICLE LOT | % EXENDIN-4 IN FORMULATION W/W ACTUAL | % EXCIPIENT IN FORMULATION W/W | DRUG PHASE (INNER AQUEOUS EMULSION) | POLYMER PHASE |
|---|---|---|---|---|
| M-28 | 2.8% | 2% SUCROSE 0.5% AMMONIUM SULFATE | Exendin-4 (50 mg/mL in water) 2% sucrose, 0.5% ammonium sulfate | 4A 50:50 |
| M-29 | 2.8% | 2% MANNITOL 0.5% AMMONIUM SULFATE | Exendin-4 (50 mg/mL in Water) 2% mannitol, 0.5% ammonium sulfate | 4A 50:50 |
| M-30 | 1.8% | 2% SUCROSE 0.5% AMMONIUM SULFATE | Exendin-4 (50 mg/mL in water) 2% sucrose, 0.5% ammonium sulfate | 4A 50:50 |
| M-31 | 1.9% | 2% MANNITOL 0.5% AMMONIUM SULFATE | Exendin-4 (50 mg/mL in water) 2% mannitol, 0.5% ammonium sulfate | 4A 50:50 |

The Microparticle Formulations described in Table 8 were prepared a second time (Formulation M-28A, M-29A, M-30A and M-31A) but using a different drying method and evaluation of the serum profile determined. The sustained release profiles for M-28A-M-31A are depicted graphically in FIG. 15.

DOE STUDY 2: Formulations containing 0.3% ammonium sulfate were evaluated. The sustained release profile for the formulations are set forth in FIG. 16. A description of the Microparticle Formulations M-32-M-35 is set forth in Table 9.

TABLE 9

| MICRO-PARTICLE LOT | % EXENDIN-4 IN FORMULATION W/W ACTUAL | % EXCIPIENT IN FORMULATION W/W | DRUG PHASE (INNER AQUEOUS EMULSION) | POLYMER PHASE |
|---|---|---|---|---|
| M-32 | 2.5% | 2% SUCROSE 0.3% AMMONIUM SULFATE | Exendin-4 (50 mg/mL in water) 2% sucrose, 0.3% ammonium sulfate | 4A 50:50 |
| M-33 | 2.66% | 2% MANNITOL 0.3% AMMONIUM SULFATE | Exendin-4 (50 mg/mL in Water) 2% mannitol, 0.3% ammonium sulfate | 4A 50:50 |
| M-34 | 1.66% | 2% MANNITOL 0.3% AMMONIUM SULFATE | Exendin-4 (50 mg/mL in water) 2% mannitol, 0.3% ammonium sulfate | 4A 50:50 |
| M-35 | 1.68% | 2% SUCROSE 0.3% AMMONIUM SULFATE | Exendin-4 (50 mg/mL in water) 2% sucrose, 0.3% ammonium sulfate | 4A 50:50 |

Example 6

Effects of Local Delivery of Secondary Agent-Containing Microparticles on the Release of Exendin-4 from Exendin-Containing Microparticles The effects on the pharmacokinetic profile of exendin-4 release following administration of exendin-4-containing microparticles co-administered to male Sprague-Dawley rats with placebo microparticles, or triamcinolone-containing microparticles was determined.

Preparation of Exendin-Containing Microparticles and Triamcinolone-Containing Microparticles Exendin-containing microparticles were prepared as described above for Selected Formulation 2 (SF-2) having 3% exendin-4 (in water), 2% sucrose and 0.5% ammonium sulfate in 4A, 50:50 PLG and Initial Formulation-1 (IF-1) having 1% exendin-4 load (50 mg/mL Exendin-4), 1% sucrose (50 mg/mL sucrose) 30 mM sodium acetate (pH 4-4.5) and 3A, 50:50 PLG.

Triamcinolone acetonide-containing microparticles (2% load) were prepared as follows: 42 mg of triamcinolone acetonide was dissolved in benzyl alcohol. The triamcinolone solution was then added to about 24.3 mL of a 6% PLG (2.5A) solution in methylene chloride. The resulting homogenous solution was added to a stirring solution of 5% PVA. The stirring rate was raised until microscopic examination of the emulsion indicated that the diameter of the droplets was about 150-75 microns. The emulsion was then slowly added to stirring cold water. After about 45 minutes of stirring, the suspension was allowed to settle at 4° C. The microparticles were collected by filtration, washed with cold water, frozen and lyophilized to dryness.

Placebo microparticles were prepared according to the process for preparation of the triamcinolone microparticles but absent the triamcinolone.

Administration of Microparticles

Microparticle administration was as follows: Animals were anesthetized fully with 5% halothane. Each animal was shaved and the back swabbed with alcohol. Exendin-4 containing microparticles and either placebo or triamcinolone-containing microparticles were suspended in vehicle and injected into the interscapular site. Treatment groups are summarized in Table 10.

A dose of 120 mg of exendin-4-containing microparticles (Formulation IF-1) plus 30 mg of placebo (Group A) or 10 mg of 2% w/w triamcinolone-containing microparticles (Group B) was administered to the rats. A dose of 40 mg of exendin-containing microparticles (Formulation SF-2) plus 30 mg of placebo (Group C) or 10 mg of 2% w/w triamcinolone-containing microparticles (Group D) was also administered to the rats. Sample collection time points were pre-bleed, 2 hrs, 6 hrs, 10 hrs, and days 1, 2, 4, 7, 10, 14, 17, 21, 24, 29, 32, 36 and 39.

Plasma Evaluation

To evaluate plasma exendin levels, 0.25 mL samples of plasma were collected via tail vein on days 0 and 1, and 0.4 mL samples were collected on the remaining days specified in Table 10 (four animals per group). The samples were centrifuged and the plasma fraction frozen (−80° C.). Plasma exendin levels were quantitated by IRMA.

Results

Plasma Exendin-4 Levels

Figure 17:
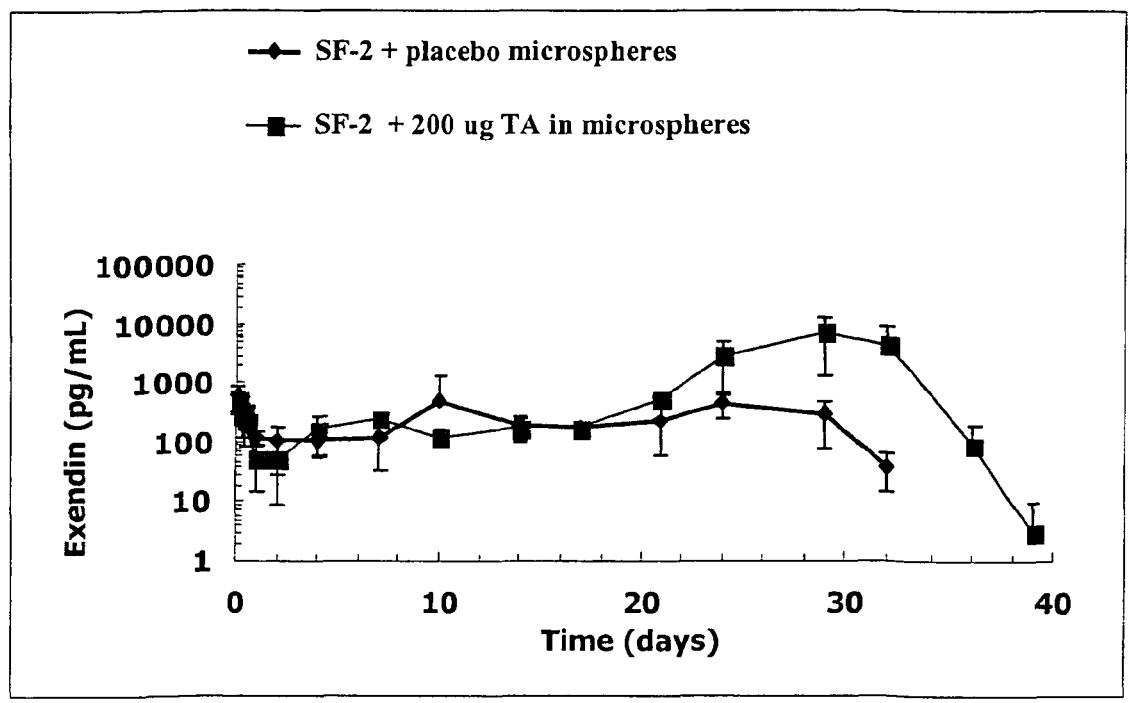
FIG. 17 is a graph of serum exendin-4 levels (pg/mL) in rats administered 120 mg of exendin-containing microparticles plus 30 mg of placebo microparticles or 10 mg of 2% triamcinolone acetonide-containing microparticles versus time in days.

FIG. 17 shows the results of the effects of exendin-4-containing microparticles co-administered with placebo microparticles and triamcinolone acetonide-containing microparticles on plasma exendin levels in the form of a graph of exendin plasma levels (pg/mL) versus time (days) post injection. As shown in FIG. 17, the pharmacokinetic profile for Group B was improved over controls (Group A). Specifically, enhanced bioavailability was observed for the triamcinolone acetonide treated group (Group B) in that plasma levels on day 32 remained detectable while this was the last day detectable for the control group. It is noted that plasma levels were still detectable at day 39 for Group B, showing a substantial increase in the duration of release of exendin when coadministered with triamcinolone acetonide-containing microparticles. $C_{ave}$ levels, $C_{max}$ and AUC were also desirably modulated as a result of coadministration of triamcinolone acetonide-containing microparticles with the exendin-containing microparticles.

Figure 18:
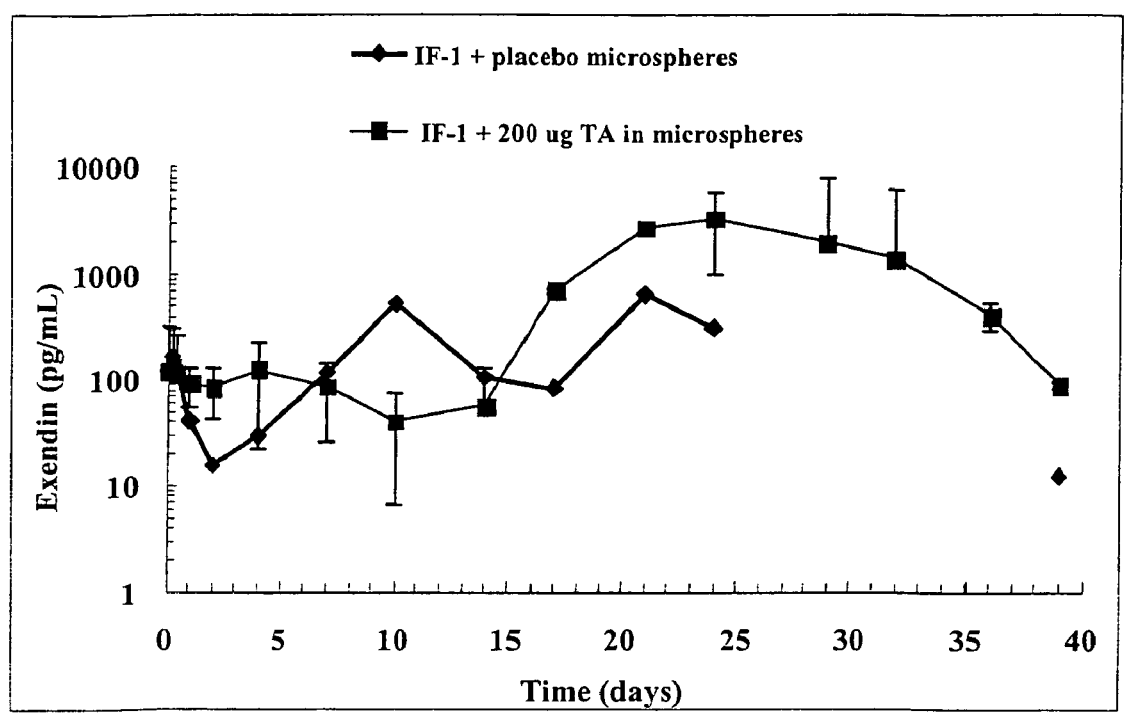
FIG. 18 is a graph of serum exendin-4 levels (pg/mL) in rats administered 40 mg of exendin-containing microparticles plus 30 mg of placebo microparticles or 10 mg of 2% triamcinolone acetonide-containing microparticles versus time in days.

FIG. 18 shows the results of the effects of exendin-containing microparticles co-administered with placebo microparticles and triamcinolone acetonide-containing microparticles on serum exendin levels in the form of a graph of exendin serum levels (pg/mL) versus time (days) post injection. As shown in FIG. 18, the pharmacokinetic profile for Group D was improved over controls, Group C. Specifically, enhanced bioavailability was observed for the triamcinolone treated group (Group D) in that plasma levels were still detectable at day 39 showing a substantial increase in the duration of release of exendin when coadministered with triamcinolone acetonide-containing microparticles in comparison to controls (Group C) which were not detectable after day 24. $C_{ave}$ levels, $C_{max}$ and AUC were also desirably modulated as a result of coadministration of triamcinolone acetonide-containing microparticles with the exendin-containing microparticles.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for the sustained release in vivo of a biologically active polypeptide, comprising:

TABLE 10

| GROUP | # ANIMALS | EXENDIN-4 MICROPARTICLES | SECONDARY AGENT | TREATMENT |
|---|---|---|---|---|
| A | 4 | 120 mg IF-1 | PLACEBO MICROPARTICLES | 30 mg |
| B | 4 | 120 mg IF-1 | 2% TRIAMCINOLONE MICROPARTICLES | 10 mg |
| C | 4 | 40 mg SF-2 | PLACEBO MICROPARTICLES | 30 mg |
| D | 4 | 40 mg SF-2 | 2% TRIAMCINOLONE MICROPARTICLES | 10 mg | administering a sustained release composition that comprises a biocompatible polymer having exendin-4 incorporated therein, and a corticosteroid present in an amount sufficient to modify the release profile of the exendin-4 from the biocompatible polymer and to provide increased bioavailability of the exendin-4, wherein the exendin-4 is released from the sustained release composition for a period of at least about two weeks.

2. The method of claim 1, wherein a weight ratio of the exendin-4 to the corticosteroid is at least 6:1.

3. The method of claim 2, wherein the corticosteroid is triamcinolone.

4. The method of claim 1, wherein the administering is carried out by injection.

5. The method of claim 1, wherein the exendin-4 is released from the sustained release composition for a period of at least about three weeks.

6. The method of claim 1, wherein the exendin-4 is released from the sustained release composition for a period of at least about four weeks.

* * * * *